United States Patent
Jeung et al.

(10) Patent No.: US 7,123,758 B2
(45) Date of Patent: Oct. 17, 2006

(54) METHOD AND SYSTEM FOR MONITORING BREATHING ACTIVITY OF A SUBJECT

(75) Inventors: Andrew Jeung, Mountain View, CA (US); Hassan Mostafavi, Los Altos, CA (US); Majid L. Riaziat, San Jose, CA (US); Robert M. Sutherland, Menlo Park, CA (US); George Zdasiuk, Portola Valley, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 487 days.

(21) Appl. No.: 10/327,603

(22) Filed: Dec. 20, 2002

(65) Prior Publication Data

US 2004/0071337 A1 Apr. 15, 2004

Related U.S. Application Data

(63) Continuation-in-part of application No. 10/305,416, filed on Nov. 25, 2002, now Pat. No. 6,980,679, which is a continuation-in-part of application No. 10/234,658, filed on Sep. 3, 2002, now Pat. No. 6,973,202, and a continuation-in-part of application No. 09/893,122, filed on Jun. 26, 2001, now Pat. No. 6,937,696, and a continuation-in-part of application No. 09/178,385, filed on Oct. 23, 1998, now Pat. No. 6,279,579, which is a continuation-in-part of application No. 09/178,383, filed on Oct. 23, 1998, now Pat. No. 6,621,889, and a continuation-in-part of application No. 09/712,724, filed on Nov. 14, 2000, now Pat. No. 6,690,965, which is a continuation of application No. 09/178,384, filed on Oct. 23, 1998, now abandoned.

(51) Int. Cl.
*G06K 9/00* (2006.01)

(52) U.S. Cl. .................. 382/128; 382/287; 600/534
(58) Field of Classification Search ................ 382/100, 382/103, 107, 128, 154, 287, 291; 600/476, 600/529, 534, 535, 536; 128/922; 348/77, 348/94, 95
See application file for complete search history.

(56) References Cited

U.S. PATENT DOCUMENTS 3,861,807 A 1/1975 Lescrenier .................. 356/152
3,871,360 A 3/1975 Van Horn et al. ...... 128/2.05 R (Continued)

FOREIGN PATENT DOCUMENTS

DE 43 41 324 A 1 6/1995

(Continued)

OTHER PUBLICATIONS

Gerig, L.H., El Hakim, S.F., Szanto, J., Salhani, D., and Girard, A., "The Development and Clinical Application of a Patient Position Monitoring System", Ottawa Regional Cancer Centre, General Division, 501 Smyth Rd., Ottawa, Ontario, Canada K1H 8L6; National Research Council, IIT, Ottawa, Ontario, Canada K1A OR6; *SPIE* vol. 2350 Videometrics III (1994); pp. 59-72.

(Continued)

*Primary Examiner*—Andrew W. Johns
(74) *Attorney, Agent, or Firm*—Bingham McCutchen LLP

(57) ABSTRACT

A method and system for monitoring breathing movement of a subject is disclosed. A method and system for detecting and predictably estimating regular cycles of breathing movements is disclosed. Another disclosed aspect of the invention is directed to detect and report irregularity of breathing activity of an infant, such as cessation and non-periodicity, which suggests a likelihood of SIDS.

27 Claims, 11 Drawing Sheets

U.S. PATENT DOCUMENTS

| | | | |
|---|---|---|---|
| 3,952,201 A | 4/1976 | Hounsfield | 250/403 |
| 4,031,884 A | 6/1977 | Henzel | 128/2.05 R |
| 4,262,306 A | 4/1981 | Renner | 358/93 |
| 4,463,425 A | 7/1984 | Hirano et al. | 364/417 |
| 4,710,717 A | 12/1987 | Pelc et al. | 324/309 |
| 4,895,160 A | 1/1990 | Reents | 128/671 |
| 4,971,065 A | 11/1990 | Pearce | 128/721 |
| 4,994,965 A | 2/1991 | Crawford et al. | 364/413.15 |
| 5,080,100 A | 1/1992 | Trotel | 128/653.1 |
| 5,271,055 A | 12/1993 | Hsieh et al. | 378/95 |
| 5,279,309 A | 1/1994 | Taylor et al. | 128/782 |
| 5,295,483 A | 3/1994 | Nowacki et al. | 128/660.03 |
| 5,315,630 A | 5/1994 | Sturm et al. | 378/65 |
| 5,389,101 A | 2/1995 | Heilbrun et al. | 606/130 |
| 5,394,875 A | 3/1995 | Lewis et al. | 128/660.09 |
| 5,396,875 A | 3/1995 | Kotwicki et al. | 123/681 |
| 5,446,548 A | 8/1995 | Gerig et al. | 356/375 |
| 5,482,042 A | 1/1996 | Fujita | 128/653.1 |
| 5,513,646 A | 5/1996 | Lehrman et al. | 128/716 |
| 5,538,494 A | 7/1996 | Matsuda | 600/1 |
| 5,565,777 A | 10/1996 | Kanayama et al. | 324/309 |
| 5,582,182 A | 12/1996 | Hillsman | 128/716 |
| 5,603,318 A | 2/1997 | Heilbrun et al. | 128/630 |
| 5,619,995 A | 4/1997 | Lobodzinski | 128/653.1 |
| 5,622,187 A | 4/1997 | Carol | 128/897 |
| 5,638,819 A | 6/1997 | Manwaring et al. | 128/653.1 |
| 5,662,111 A | 9/1997 | Cosman | 128/653.1 |
| 5,662,112 A | 9/1997 | Heid | 128/653.2 |
| 5,727,554 A | 3/1998 | Kalend et al. | 128/653.1 |
| 5,764,723 A | 6/1998 | Weinberger et al. | 378/65 |
| 5,771,310 A | 6/1998 | Vannah | 382/154 |
| 5,784,431 A | 7/1998 | Kalend et al. | 378/65 |
| 5,820,553 A | 10/1998 | Hughes | 600/426 |
| 5,823,192 A | 10/1998 | Kalend et al. | 128/845 |
| 5,836,954 A | 11/1998 | Heilbrun et al. | 606/130 |
| 5,912,656 A | 6/1999 | Tham et al. | 345/112 |
| 5,954,647 A | 9/1999 | Bova et al. | 600/407 |
| 5,993,397 A | 11/1999 | Branson | 600/534 |
| 6,076,005 A | 6/2000 | Sontag et al. | 600/413 |
| 6,138,302 A | 10/2000 | Sashin et al. | 5/600 |
| 6,144,874 A | 11/2000 | Du | 600/413 |
| 6,144,875 A | 11/2000 | Schweikard et al. | 600/427 |
| 6,146,390 A | 11/2000 | Heilbrun et al. | 606/130 |
| 6,165,181 A | 12/2000 | Heilbrun et al. | 606/130 |
| 6,185,445 B1 | 2/2001 | Knüttel | 600/411 |
| 6,185,446 B1 | 2/2001 | Carlsen, Jr. | 600/411 |
| 6,198,959 B1 | 3/2001 | Wang | 600/413 |
| 6,272,368 B1 | 8/2001 | Alexandrescu | 600/407 |
| 6,296,613 B1 | 10/2001 | Emmenegger et al. | 600/459 |
| 6,300,974 B1 | 10/2001 | Viala et al. | 348/61 |
| 6,348,058 B1 | 2/2002 | Melkent et al. | 606/130 |
| 6,370,217 B1 | 4/2002 | Hu et al. | 378/8 |
| 6,405,072 B1 | 6/2002 | Cosman | 600/426 |
| 6,434,507 B1 | 8/2002 | Clayton et al. | 702/152 |
| 6,473,635 B1 | 10/2002 | Rasche | 600/428 |
| 6,501,981 B1 | 12/2002 | Schweikard et al. | 600/427 |
| 6,527,443 B1 | 3/2003 | Vilsmeier et al. | 378/205 |
| 6,621,889 B1 | 9/2003 | Mostafavi | 378/65 |
| 6,661,617 B1 | 12/2003 | Hipwell, Jr. et al. | 360/294.4 |
| 6,665,370 B1 | 12/2003 | Bruder et al. | 378/15 |
| 6,724,930 B1 | 4/2004 | Kosaka et al. | 382/154 |
| 2002/0023652 A1 | 2/2002 | Riaziat et al. | 128/897 |
| 2003/0007593 A1 | 1/2003 | Heuscher et al. | 378/4 |
| 2003/0063292 A1 | 4/2003 | Mostafavi | 356/614 |
| 2003/0072419 A1 | 4/2003 | Bruder et al. | 378/210 |
| 2003/0210812 A1 | 11/2003 | Khamene et al. | 382/128 |
| 2004/0005088 A1 | 1/2004 | Jeung et al. | 382/128 |
| 2004/0116804 A1 | 6/2004 | Mostafavi | 600/428 |
| 2004/0218719 A1 | 11/2004 | Brown et al. | 378/95 |

FOREIGN PATENT DOCUMENTS

| | | |
|---|---|---|
| FI | 79458 B | 9/1989 |
| WO | WO 98/16151 A1 | 4/1998 |
| WO | WO 98/38908 A1 | 9/1998 |

OTHER PUBLICATIONS

Baroni, Guido; Ferrigno, Giancarlo, Real-time Motion Analysis for Definition and Control of Patient Postion in Radiotherapy, *SPIE*, vol. 2709; 0-81942084-8/96; pp. 506-515.

Lopresti, B.J.; Russo, A., Jones, W.F., et al., "Implementation and Performance of an Optical Motion Tracking System for High Resolution Brain PET Imaging"; *IEEE Transactions on Nuclear Science*, vol. 46, No. 6, Dec. 1999; pp. 2065-2067.

International Search Report, Varian Medical Systems, Inc., PCT/US03/27552, Feb. 19, 2004.

Adams, W.B. et al. "Correlator Compensation Requirements for Passive Time-Delay Estimation with Moving Source or Receivers" IEEE (Apr. 1980) ASSP-28(2):158-168.

Bankman, I.N. et al. "Optimal Detection, Classification, and Superposition Resolution in Neural Waveform Recordings" IEEE (Aug. 1993) 40(8):836-841).

Fee, M.S. et al. "Automatic Sorting of Multiple Unit Neuronal Signals in the Presence of Anisotropic and non-Gaussian Variability" J. Neuroscience Methods (1996) 69:175-188.

Nevatia, R. et al. "Human Body Tracking with Articulated Human Body Model" (Nov. 2002) pp. 1-3.

Paradis, A.L. et al. "Detection of Periodic Signals in Brain Echo-Planar Functional Images" IEEE (Jan. 1, 1997) pp. 696-697.

Paivansalo Suramo, M. et al. "Cranio-Caudal Movements of the Liver, Pancreas and Kidneys in Respiration" Acta Radiol. Diagn. 2 (1984) pp. 129-131.

Preliminary Search Brochure entitled "Kinematic Measurement Systems" by Qualisys printed Apr. 4, 1994.

International Search Report for PCT/US03/36454 issued May 28, 2004.

Josefsson, T. et al. "A Flexible High-Precision Video System for Digital Recording of Motor Acts Through Lightweight Reflex Markers" *Computer Methods & Programs in Biomedicine* (1996) 49:119-129.

Lee, M.W. and I. Cohen "Human Body Tracking with Auxiliary Measurements" *IEEE International Workshop on Analysis and Modeling of Faces and Gestures* (2003) 8 pgs., located at http://iris.usc.edu/~icohen/projects/human/body/index.htm.

Ahlström, K. H. et al. "Pulmonary MR Angiography with Ultrasmall Superparamagnetic Iron Oxide Particles as a Blood Pool Agent and a Navigator Echo for Respiratory Gating: Pilot Study" *Radiology* (Jun. 1999) 211(3):865-869.

Axel, L. et al. "Respiratory Effects in Two-Dimensional Fourier Transform MR Imaging" *Radiology* (Sep. 1986) 160(3):795-801.

Danias, P.G. et al. "Prospective Navigator Correction of Image Position for Coronary MR Angiography" *Radiology* (Jun. 1997) 203:733-736.

Du, Y.P. et al. "A comparison of prospective and retrospective respiratory navigator gating in 3D MR coronary angiography" *Int'l J. Cardiovascular Imaging* (2001) 17:287-294.

Du, Y.P. "Prospective navigator gating with a dual acceptance window technique to reduce respiratory motion artifacts in 3D MR coronary angiography" *Int'l J. Cardiovascular Imaging* (2003) 19:157-162.

Felblinger, J. et al. "Effects of physiologic motion of the human brain upon quantitative $^{1}$H-MRS: analysis and correction by retrogating" *NMR in Biomedicine* (1998) 11:107-114.

Fishbein, K.W. et al. "The lever-coil: a simple, inexpensive sensor for respiratory and cardiac motion in MRI experiments" *Magnetic Resonance Imaging* (2001) 19:881-889.

Haacke, E.M. and G.w. Lenz "Improving MR Image Quality in the Presence of Motion by Using Rephasing Gradients" *AJR* (Jun. 1987) 148:1251-1258.

Huber, A. et al. "Navigator Echo-Based Respiratory Gating for Three-Dimensional MR Coronary Angiography: Results from Healthy Volunteers and Patients with Proximal Coronary Artery Stenoses" *AJR* (Jul. 1999) 173:95-101.

Lieberman, J.M. et al. "Gated Magnetic Resonance Imaging of the Normal Diseased Heart" *Radiology* (Aug. 1984) 152:465-470.

Manke, D. et al. "Respiratory Motion in Coronary Magnetic Resonance Angiography: A Comparison of Different Motion Models" *J. Magnetic Resonance Imaging* (2002) 15:661-671.

Manke, D. et al. "Model Evaluation and Calibration for Prospective Respiratory Motion Correction in Coronary MR Angiography Based on 3-D Image Registration" *IEEE Transactions on Medical Imaging* (Sep. 2002) 21(9):1132-1141.

McConnell, M.V. et al. "Comparison of Respiratory Suppression Methods and Navigator Locations for MR Coronary Angiography" *AJR* (May 1997) 168:1369-1375.

McConnell, M.V. et al. "Prospective Adaptive Navigator Correction for Breath-Hold MR Coronary Angiography" *MRM* (1997) 37:148-152.

Nikolaou, K. et al. "Navigator Echo-Based Respiratory Gating for Three-Dimensional MR Coronary Angiography: Reduction of Scan Time Using a Slice Interpolation Technique" *J. Computer Assisted Tomography* (2001) 25(3):378-387.

Plein, S. et al. "Three-Dimensional Coronary MR Angiography Performed with Subject-Specific Cardiac Acquisition Windows and Motion-Adapted Respiratory Gating" *AJR* (Feb. 2003) 180:505-512.

Post, J.C. et al. "Three-Dimensional Respiratory-Gated MR Angiography of Coronary Arteries: Comparison with Conventional Coronary Angiography" *AJR* (Jun. 1996) 166:1399-1404.

Regenfus, M. et al. "Comparison of Contrast-Enhanced Breath-Hold and Free-Breathing Respiratory-Gated Imaging in Three-Dimensional Magnetic Resonance Coronary Angiography" *Am. J. Cardiology* (Oct. 1, 2002) 90:725-730.

Schär, M. et al. "The Impact of Spatial Resolution and Respiratory Motion on MR Imaging of Atherosclerotic Plaque" *J. Magnetic Resonance Imaging* (2003) 17:538-544.

Spuentrup, E. et al. "Respiratory motion artifact suppression in diffusion-weighted MR imaging of the spine" *Eur. Radiol.* (2003) 13:330-336.

Thickman, D. et al. "Phase-Encoding Direction upon Magnetic Resonance Image Quality of the Heart" *Magnetic Resonance in Medicine* (1988) 6:390-396.

Wang, Y. et al. "Navigator-Echo-based Real-Time Respiratory Gating and Triggering for Reduction of Respiration Effects in Three-dimensional Coronary MR Angiography" *Radiology* (1996) 198:55-60.

Weber, C. et al. "Correlation of 3D MR coronary angiography with selective coronary angiography: feasibility of the motion adapted gating technique" *Eur. Radiol.* (2002) 12:718-726.

Wiesmann, F. "High-Resolution MRI with Cardiac and Respiratory Gating Allows for Accurate In Vivo Atherosclerotic Plaque Visualization in the Murine Aortic Arch" *Magnetic Resonance in Medicine* (2003) 50:69-74.

Wood, M.L. and R.M. Henkelman "Suppression of respiratory motion artifacts in magnetic resonance imaging" *Med. Phys.* (Nov./Dec. 1996) 13(6):794-805.

Worthley, S.G. et al. "Cardiac gated breath-hold back blood MRI of the coronary artery wall: An in vivo and ex vivo comparison" *Int'l J. Cardiovascular Imaging* (2001) 17:195-201.

Yamashita, Y. et al. "MR Imaging of Focal Lung Lesions: Elimination of Flow and Motion Artifact by Breath-Hold ECG-Gated and Black-Blood Techniques on T2-Weighted Turbo SE and STIR Sequences" *J. Magnetic Resonance Imaging* (1999) 9:691-698.

Balter, J.M., et al.; "Uncertainties In CT-Based Radiation Therapy Treatment Planning Associated With Patient Breathing"; *Int. J. Radiat. Oncol., Biol., Phys.* 36; pp. 167-174 (Aug. 1996).

Bellenger, N.G., et al.; "Left Ventricular Quantification In Heart Failure By Cardiovascular MR Using Prospective Respiratory Navigator Gating: Comparison With Breath-Hold Acquisition"; *J. Magn. Reson. Imaging* 11; pp. 411-417; (Apr. 2000).

Cho, K., et al.; "Development Of Respiratory Gated Myocardial SPECT System"; *J. Nucl. Cardiol.* 6; pp. 20-28; (Jan./Feb. 1999).

Davies, S.C., et al.; "Ultrasound Quantitation Of Respiratory Organ Motion in The Upper Abdomen"; *Br. J. Radiol.* 67; pp. 1096-1102 (Nov. 1994).

Ehman, R.L., et al.; "Magnetic Resonance Imaging With Respiratory Gating: Techniques and Advantages"; *Am. J. Roentgenol* 143; pp. 1175-1182 (Dec. 1984).

Frölich, H., et al.; "A Simple Device For Breath-Level Monitoring During CT"; *Radiology* 156; p. 235 (Jul. 1985).

Hanley, J., et al.; "Deep Inspiration Breath-Hold Technique For Lung Tumors: The Potential Value of Target Immobilization And Reduced Lung Density In Dose Escalation"; *Int. J. Radiat. Oncol., Biol. Phys.* 45; pp. 603-611 (Oct. 1999).

Henkelman, R.M., et al.; "How Important Is Breathing In Radiation Therapy Of The Thorax?"; *Int. J. Radiat. Oncol., Biol. Phys.* 8; pp. 2005-2010 (Nov. 1982).

Hofman, M.B.M., et al.; "MRI Of Coronary Arteries: 2D Breath-Hold vs. 3D Respiratory-Gated Acquisition"; *J. of Comp. Assisted Tomography* 19; pp. 56-62 (Jan./Feb. 1995).

Iwasawa, T., et al.; "Normal In-Plane Respiratory Motion of the Bilateral Hemidiaphragms Evaluated By Sequentially Subtracted Fast Magnetic Resonance Images"; *Journal of Thoracic Imaging*; 1999; vol. 14, No. 2; pp. 130-134.

Johnson, L. S., et al.; "Initial Clinical Experience With A Video-Based Patient Positioning System"; *Int. J. Radiat. Oncol., Biol. Phys.* 45; pp. 205-213; (Aug. 1999).

Jolesz, F., M.D.; "Image-Guided Procedures and the Operating Room of the Future"; *Radiology; SPL Technical Report* #48; May 1997; 204; pp. 601-612.

Kachelriess, M., et al.; "Electrocardiogram-correlated Image Reconstruction From Subsecond Spiral Computed Tomography Scans Of The Heart"; *Med. Phys.* 25(12); Dec. 1998; pp. 2417-2431.

Keatley, E., et al.; "Computer Automated Diaphragm Motion Quantification in a Fluoroscopic Movie"; *Dept. of Medical Physics, Memorial Sloan-Kettering Cancer Center, New York*; 3 pps..

Kim, W.S., et al.; "Extraction of Cardiac and Respiratory Motion Cycles by Use of Projection Data and its Applications to NMR Imaging"; *Magnetic Resonance in Medicine* 13; 1990; pp. 25-37.

Korin, H.W., et al.; "Respiratory Kinematics Of The Upper Abdominal Organs: A Quantitative Study"; *Magn. Reson. Med.* 23; pp. 172-178 (Jan. 1992).

Kubo, H. D., et al.; "Breathing-Synchronized Radiotherapy Program at the University of California Davis Cancer Center"; *Med. Phys.* 27(2); Feb. 2000; pp. 346-353.

Kubo, H. D., et al.; "Potential and Role of a Prototype Amorphous Silicon Array Electronic Portal Imaging Device in Breathing Synchronized Radiotherapy"; *Med. Phys.* 26(11); Nov. 1999; pp. 2410-2414.

Kubo, H.D., et al.; "Compatibility Of Varian 2100C Gated Operations With Enhanced Dynamic Wedge And IMRT Dose Delivery"; *Med. Phys.* 27; pp. 1732-1738; (Aug. 2000).

Kubo, H. D., et al.; "Respiration Gated Radiotherapy Treatment: A Technical Study"; *Phys. Med. Biol.* (1996) vol. 41; pp. 83-91.

Kutcher, G.J., et al.; "Control, Correction, and Modeling Of Setup Errors and Organ Motion", *Semin. Radiat. Oncol.* 5; pp. 134-145 (Apr. 1995).

Lethimonnier, F., et al.; "Three-Dimensional Coronary Artery MR Imaging Using Prospective Real-Time Respiratory Navigator And Linear Phase Shift Processing: Comparison With Conventional Coronary Angiography"; *Magn. Reson. Imaging* 17; pp. 1111-1120; (1999).

Lewis, C.E., et al.; "Comparison Of Respiratory Triggering And Gating Techniques For The Removal Of Respiratory Artifacts In MR Imaging"; *Radiology* 160; pp. 803-810; (Sep. 1986).

Li, D., et al.; "Coronary Arteries: Three-dimensional MR Imaging With Retrospective Respiratory Gating"; *Radiology*; Dec. 1996; vol. 201; No. 3; pp. 857-863.

Luker, G. D., et al.; "Ghosting of Pulmonary Nodules With Respiratory Motion: Comparison of Helical and Conventional CT Using an In Vitro Pediatric Model"; *AJR:167*; Nov. 1996; pp. 1189-1193.

Mageras, G., et al.; "Initial Clinical Evaluation Of A Respiratory Gating Radiotherapy System"; 22nd *Annual EMBS International Conference, Chicago, IL.*; pp. 2124-2127; (Jul. 23-28, 2000).

Mageras, G.S., et al.; "Respiratory Motion-Induced Treatment Uncertainties"; *Patras Medical Physics 99—VI International Conference On Medical Physics, Monduzzi Editore*; pp. 33-39; (Sep. 1999).

Mageras, G.S.; "Interventional Strategies For Reducing Respiratory-Induced Motion In External Beam Therapy"; *The Use of Computers In Radiation Therapy XIIIth International Conference, Heidelberg, Germany*; pp. 514-516; (May 2000).

Mah, D., et al.; "Technical Aspects Of The Deep Inspiration Breath Hold Technique In The Treatment Of Thoracic Cancer"; *Int. J. Radiat. Oncol., Biol., Phys.* 48; pp. 1175-1185; (Nov. 2000).

Mah, K., et al.; "Time Varying Dose Due To Respiratory Motion During Radiation Therapy Of The Thorax"; *Proceedings of the Eighth Int'l Conference on the Use of Computers In Radiation Therapy*; Toronto, Canada; Jul. 9-12, 1984; pp. 294-298.

Malone, S., et al.; "Respiratory-Induced Prostate Motion: Quantification And Characterization", *Int. J. Radiat. Oncol., Biol., Phys.* 48; pp. 105-109; (Aug. 2000).

Moreland, M.A., et al.; "The Influence Of Respiration Induced Motion Of The Kidneys On The Accuracy Of Radiotherapy Treatment Planning, A Magnetic Resonance Imaging Study"; *Radiotherapy Oncol.* 30, pp. 150-154 (1994).

Mori, M., et al.; "Accurate Contiguous Sections Without Breath-Holding On Chest CT: Value of Respiratory Gating and Ultrafast CT"; *AJR:162*, May 1994; pp. 1057-1062.

Ohara, K., et al.; "Irradiation Synchronized With Respiration Gate"; *Int. J. Radiat. Oncol., Biol. Phys.* 17; pp. 853-857; (Oct. 1989).

Oshinski, J.N., et al.; "Two-Dimensional Coronary MR Angiography Without Breath Holding"; *Radiology* 201; pp. 737-743; (Dec. 1996).

Peltola, S.M.,; "Gated Radiotherapy To Compensate For Patient Breathing"; *Proceedings of the Eleventh Varian Users Meeting*; Marco Island, Florida; May 11-13, 1986.

Ramsey, C.R., et al.; "A Comparison Of Beam Characteristics For Gated And Nongated Clinical X-Ray Beams"; *Med. Phys.* 26; pp. 2086-2091; (Oct. 1999).

Ramsey, C.R., et al.; "Clinical Efficacy Of Respiratory Gated Conformal Radiation Therapy"; *Med. Dosim.* 24; pp. 115-119; (1999).

Ritchie, C. J., et al.; "Predictive Respiratory Gating: A New Method To Reduce Motion Artifacts on CT Scans"; *Radiology*; 1994; pp. 847-852; vol. 190; No. 3.

Robinson, T.E., et al.; "Standardized High-Resolution CT of the Lung Using A Spirometer-Triggered Electron Beam CT Scanner"; *AJR:172*; Jun. 1999; pp. 1636-1638.

Rogus, R.D., et al.; "Accuracy Of A Photogrammetry-Based Patient Positioning and Monitoring System For Radiation Therapy"; *Med. Phys.* 26; pp. 721-728; (May 1999).

Rosenzweig, K.E., et al.; "The Deep Inspiration Breath Hold Technique In The Treatment Of Inoperable Non-Small Cell Lung Cancer"; *Int. J. Radiat. Oncol., Biol., Phys.* 48; pp. 81-87; (Aug. 2000).

Ross, C.S., et al.; "Analysis Of Movement Of Intrathoracic Neoplasms Using Ultrafast Computerized Tomography"; *Int. J. Radiat. Oncol., Biol., Phys.* 18; pp. 671-677; (Mar. 1990).

Runge, V.M., et al.; "Respiratory Gating In Magnetic Resonance Imaging at 0.5 Tesla"; *Radiology* 151; pp. 521-523; (May 1984).

Sachs, T.S., et al.; "Real-Time Motion Detection In Spiral MRI Using Navigators"; *Magn. Reson. Med.* 32; pp. 639-645; (Nov. 1994).

Schwartz, L.H., et al.; "Kidney Mobility During Respiration"; *Radiother. Oncol.* 32; pp. 84-86; (1994).

Shirato, H., et al.; "Four-Dimensional Treatment Planning And Fluroscopic Real-Time Tumor Tracking Radiotherapy For Moving Rumor"; *Int. J Radiat. Oncol., Biol., Phys.* 48; pp. 435-442; (Sep. 2000).

Sinkus, R., et al.; "Motion Pattern Adapted Real-Time Respiratory Gating"; *Magnetic Resonance in Medicine* 41; 1999; pp. 148-155.

Solberg, T. D., et al.; "Feasibility of Gated IMRT"; 3 pps.

Suramo, M. P., et al.; "Cranio-caudal Movements Of The Liver, Pancreas And Kidneys In Respiration", *Acta Radiol. Diagn.* 2; pp. 129-13 1; (1984).

Tada, T., et al.; "Lung Cancer: Intermittent Irradiation Synchronized With Respiratory Motion-Results Of A Pilot Study"; *Radiology*; Jun. 1998; vol. 207; No. 3; pp. 779-783.

van Geuns, R.J., et al.; "Magnetic Resonance Imaging Of The Coronary Arteries: Clinical Results From Three Dimensional Evaluation Of A Respiratory Gated Technique", *Heart* 82; pp. 515-519; (Oct. 1999).

Wang, Yi, et al.; "Implications For The Spatial Resolution In Coronary Imaging"; *Magnetic Resonance in Medicine* 33; 1995; pp. 713-719.

Weiger, M., et al.; "Motion-Adapted Gating Based on k-Space Weighting For Reduction of Respiratory Motion Artifacts"; *Magnetic Resonance In Medicine* 38; 1997; pp. 322-333.

Wong, J. W., et al.; "The Use Of Active Breathing Control (ABC) To Reduce Margin For Breathing Motion"; *Int. J. Radiation Oncology Biol. Phys.*; 1999; vol. 44; No. 4; pp. 911-919.

Woodard, P. K., et al.; "Detection of Coronary Stenoses on Source and Projection Images Using Three-Dimensional MR Angiography With Retrospective Respiratory Gating: Preliminary Experience"; *AJR:170*; Apr. 1998; No. 4; pp. 883-888.

Yorke, E., et al.; "Respiratory Gating Of Sliding Window IMRT"; 22nd Annual EMBS International Conference, Chicago, IL.; pp. 2118-2121; (Jul. 23-28, 2000).

Yuan, Q., et al.; "Cardiac-Respiratory Gating Method For Magnetic Resonance Imaging Of The Heart"; *Magn. Reson. Med.* 43; pp. 314-318; (Feb. 2000).

METHOD AND SYSTEM FOR MONITORING BREATHING ACTIVITY OF A SUBJECT

CROSS-REFERENCE TO RELATED APPLICATIONS

The present application is a continuation-in-part of U.S. application Ser. No. 10/305,416 filed Nov. 25, 2002, now U.S. Pat. No. 6,980,679, which is a continuation-in-part of U.S. application Ser. No. 10/234,658 filed Sep. 3, 2002, now U.S. Pat. No. 6,973,202, and U.S. application Ser. No. 09/893,122 filed Jun. 26, 2001, now U.S. Pat. No. 6,937,696, which is a continuation-in-part of U.S. application Ser. No. 09/178,383 filed Oct. 23, 1998, now U.S. Pat. No. 6,621,889, Ser. No. 09/178,385 filed Oct. 23, 1998, now U.S. Pat. No. 6,279,579, issued on Aug. 28, 2001, and Ser. No. 09/712,724 fled Nov. 14, 2000, now U.S. Pat. No. 6,690,965, which is a continuation of Ser. No. 09/178,384 filed Oct. 23, 1998, now abandoned, all of which are hereby incorporated by reference in their entirety.

BACKGROUND AND SUMMARY

The present invention relates to medical methods and systems. More particularly, the invention relates to a method and system for monitoring breathing activity.

A serious concern for parents of a newborn is the possibility of death by Sudden Infant Death Syndrome (SIDS). SIDS is commonly known as the sudden death of an infant under one year of age which remains unexplained after a thorough case investigation, including performance of a complete autopsy, examination of the death scene, and review of the clinical history. A SIDS death occurs quickly and is often associated with sleep, with no signs of suffering.

Although exact causes of SIDS are still unknown, mounting evidence suggests that some SIDS babies are born with brain abnormalities that make them vulnerable to sudden death during infancy. Studies of SIDS victims reveal that some SIDS infants have abnormalities in the "arcuate nucleus," a portion of the brain that is likely to be involved in controlling breathing during sleep. However, scientists believe that the abnormalities that are present at birth may not be sufficient to cause death. Other factors, such as lack of oxygen and excessive carbon dioxide intake, may also contribute to the occurrence of SIDS. During sleep, a baby can experience a lack of oxygen and excessive carbon dioxide levels when they re-inhale the exhaled air. Normally, an infant can sense such inadequate air intake, and his breathing movement can change accordingly to compensate for the insufficient oxygen and excess carbon dioxide. As such, certain types of irregularity in an infant's breathing activity can be an indicator of SIDS or the likelihood of SIDS.

Therefore, monitoring of an infant's breathing activity for breathing irregularities could help prevent or detect the possibility of SIDS. One approach to monitor the breathing activity is to attach to the body of the infant a battery-powered electronic device that can mechanically detect the breathing movement. Although such device can monitor the infant's breathing directly, the battery can render the device large and heavy, which encumbers the tiny infant. Additionally, difficulty of attachment can be expected under this approach.

Another approach to monitor an infant's breathing activity is to install a pressure sensitive pad underneath the mattress where the infant is sleeping. The pad monitors the baby's breathing activity by measuring body movement. However, because the pad is unable to directly monitor the breathing movement, accuracy of the generated breathing data can be affected.

In contrast to the above approaches, the present invention provides an improved system and method that can monitor breathing activity without creating encumbrances. With respect to infants, by continuously monitoring breathing movement during sleep and reporting detected irregularity, the present system and method can reduce the occurrence of SIDS.

In an embodiment, an optical-based system, comprising at least one camera, a marker, a computing device to compute the position of the marker, and a reporting device to transmit an alert signal, is employed to measure and record an infant's breathing movement and report detected irregularity. The system can produce breathing pattern by tracking the movement of the marker, which is placed in a particular location such that motion of the marker relates to the breathing movement of the infant. In one embodiment, the movement of multiple markers are tracked.

According to an embodiment, a method for identifying breathing pattern of an infant comprises the steps of first co-locating the marker with the infant, viewing the marker with at least one camera, producing image coordinates for the identified marker viewed by the camera, comparing the image coordinates with reference coordinates for the marker, and thereafter determining breathing motion of the infant. The computing device can analyze the breathing pattern and actuate the reporting device if irregularity is detected. Irregularity includes, but not limited to, lack of periodicity in the breathing pattern and cease of the breathing motion. Multiple markers associated with multiple infants or patients may be simultaneously monitored using the present system and method. In addition, the present approaches can be used to monitor any object, including adult patients and non-human creatures.

These and other aspects, objects, and advantages of the invention are described below in the detailed description, drawings, and claims.

BRIEF DESCRIPTION OF THE DRAWINGS

The accompanying drawings are included to provide a further understanding of the invention and, together with the Detailed Description, serve to explain the principles of the invention.

FIG. 6b depicts a front view of the camera of FIG. 6a.

FIG. 7b depicts a cross-sectional view of the retro-reflective marker of FIG. 7a.

DETAILED DESCRIPTION

An aspect of an embodiment of the present invention comprises a method for detecting periodicity and irregularity in the respiration activity of an infant. Also disclosed are embodiments of systems and devices for detecting and reporting irregularity in the respiration activity of an infant.

System for Infant Breathing Monitoring

Figure 1:
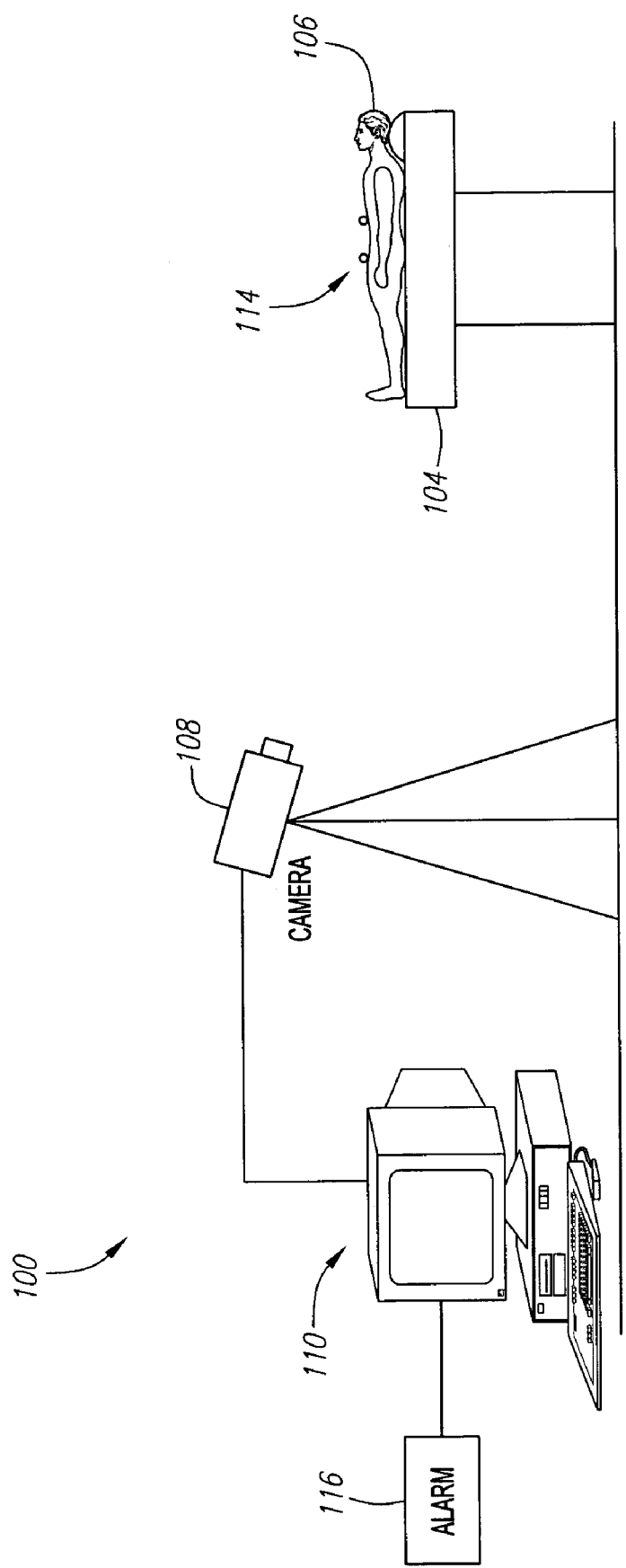
FIG. 1 depicts the components of a system for monitoring an infant's breathing activity according to an embodiment of the invention.

FIG. 1 depicts the components of an embodiment of a system 100 for monitoring an infant's breathing movement, in which data representative of the breathing movement is collected with an optical imaging apparatus. An optical or video image apparatus, such as camera 108, is aimed such that at least part of an infant 106 is within the camera's field of view. Camera 108 monitors infant 106 for motion relating to the breathing activity. For instance, camera 108 can be configured to monitor the motion of the infant's chest. According to an embodiment, camera 108 is placed on the ceiling, wall, or other support structure with its axis tilted down between 20 and 70 degrees relative to the horizontal longitudinal axis of the infant 106. In one embodiment, the camera 108 is directly mounted to the end of a crib or infant support structure. Additionally, the video image field of view is set to view an approximately 30 cm by 30 cm area of the infant's chest. For purposes of illustration only, a single camera 108 is shown in FIG. 1. However, the number of cameras 108 employed in the present invention can exceed that number.

In an embodiment, one illumination source per camera (which is an infrared source in the preferred embodiment) projects light at the infant 106 on bed 104. The generated light is reflected from one or more landmarks on the infant's body. The camera 108, which is directed at infant 106, captures and detects the reflected light from the one or more landmarks, which are preferably located on one or more locations on the infant's chest and can be viewed by camera 108.

The output signals of camera 108 are sent to a computer 110 or other type of processing unit having the capability to receive video images. According to a particular embodiment, computer 110 includes a video frame grabber card having a separate channel for each video source utilized in the system. The images recorded by camera 108 are sent to computer 110 for processing. If camera 108 produces an analog output, the frame grabber converts the camera signals to a digital signal prior to processing by computer 110.

Based upon the video signals received and analyzed by computer 110, computer 110 can send control signals to operate an alarm device 116.

Alarm device 116 can be built into or separated from computer 110. In one embodiment, upon receiving a control signal from computer 110, alarm device 116 can transmit an alarm signal, either audible, visible or both, to warn the infant's caregiver or parents of a likelihood of SIDS. Note that an alarm signal can also be transmitted to awaken infant 106 to further reduce the occurrence of SIDS. For the purpose of illustration only, FIG. 1 depicts one alarm device 116 that is connected to computer 110 through wired connection. However, a wireless connection can be used in place of or in conjunction with the wired connection. Additionally, the number of alarm devices 116 used in the present invention can vary. As an example, alarm device 116 can be installed in a plurality of locations to maximize the chance that the infant's caregiver or parents are alerted when an alarm signal is transmitted.

According to one embodiment, one or more passive markers 114 are located on the infant in the area to be detected for breathing movement. Each marker 114 preferably comprises a reflective or retro-reflective material that can reflect light, whether in the visible or invisible wavelengths. If the illumination source is co-located with camera 108, then marker 114 preferably comprises a retro-reflective material that reflects light mostly in the direction of the illumination source. Alternatively, each marker 114 comprises its own light source. The marker 114 is used in place of or in conjunction with physical landmarks on the infant's body that is imaged by the camera 108 to detect breathing movement of the infant. Markers 114 are preferably used instead of body landmarks because such markers 114 can be detected and tracked more accurately via the video image generated by camera 108. Because of the reflective or retro-reflective qualities of the preferred markers 114, the markers 114 inherently provide greater contrast in a video image to a light detecting apparatus such as camera 108, particularly when the camera 108 and illumination source are co-located. Markers 114 can be placed on clothing, outer coverings or blankets, or directly upon the infant 106.

Utilizing a video or optical based system to track the breathing movement provides several advantages. For example, a video or optical based system provides a reliable mechanism for repeating measurement results between uses on a given infant. In addition, the method of the invention is noninvasive, and even if markers are used, no cables or connections must be made to the infant. Moreover, if the use of markers is impractical, the system can still be utilized without markers by performing measurements of respiration activity keyed to selected body landmarks. The method of the invention is also more accurate because it is based upon direct and absolute measurement of external anatomical physical movement. Therefore, the present optical-based system is particularly suitable for monitoring the breathing movement and position of infants, for which intrusive/cumbersome equipment should not be used.

A possible inefficiency in tracking the markers 114 is that the marker may appear anywhere on the video frame, and all of the image elements of the video frame may have to be examined to determine the location of the marker 114. Thus, in an embodiment, the initial determination of locations for the marker 114 involves an examination of all of the image elements in the video frame. If the video frame comprises 640 by 480 image elements, then all 307200 (640*480) image elements are initially examined to find the location of the markers 114.

For real-time tracking of the marker 114, examining every image element for every video frame to determine the location of the marker 114 in real-time could consume a significant amount of system resources. Thus, in an embodiment, the real-time tracking of marker 114 can be facilitated by processing a small region of the video frame, referred to herein as a "tracking gate," that is placed based on estimation of the location of the already-identified marker 114 in a previous video frame. The previously determined location of a marker 114 defined in the previous video frame is used to define an initial search range (i.e., the tracking gate) for that same marker in real-time. The tracking gate is a relatively small portion of the video frame that, in one embodiment, is centered at the previous location of the marker 114. The tracking gate is expanded only if the tracking algorithm can not locate the marker 114 within the gate. As an example, consider the situation when the previously determined location of the center or a portion of a particular marker is image element (50,50) in a video frame. If the tracking gate is limited to a 50 by 50 area of the video frame, then the tracking gate for this example would comprise the image elements bound within the area defined by the coordinates (25,25), (25,75), (75,25), and (75,75). The other portions of the video frame are searched only if the marker 114 is not found within this tracking gate.

Figure 2:
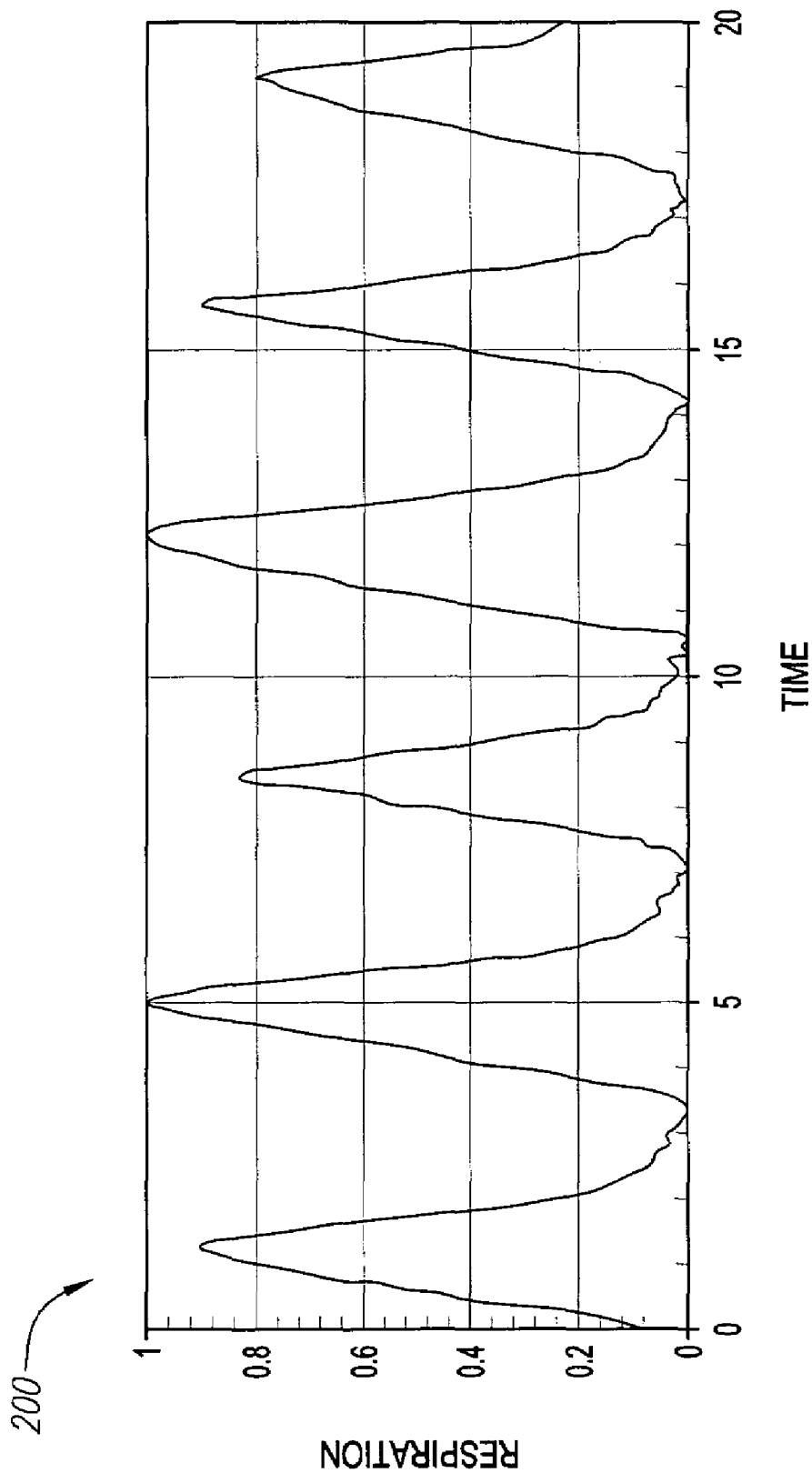
FIG. 2 depicts an example of a respiratory motion signal chart.

The video image signals sent from camera 108 to computer 110 are used to generate and track motion signals representative of the movement of marker 114 and/or landmark structures on the infant's body. FIG. 2 depicts an example of a motion signal chart 200 for respiratory movement that contains information regarding the movement of marker 114 during a given measurement period. The horizontal axis represents points in time and the vertical axis represents the relative location or movement of the marker 114. According to an embodiment, the illustrated signal in FIG. 2 comprises a plurality of discrete data points plotted along the motion signal chart 200.

Figure 6A:
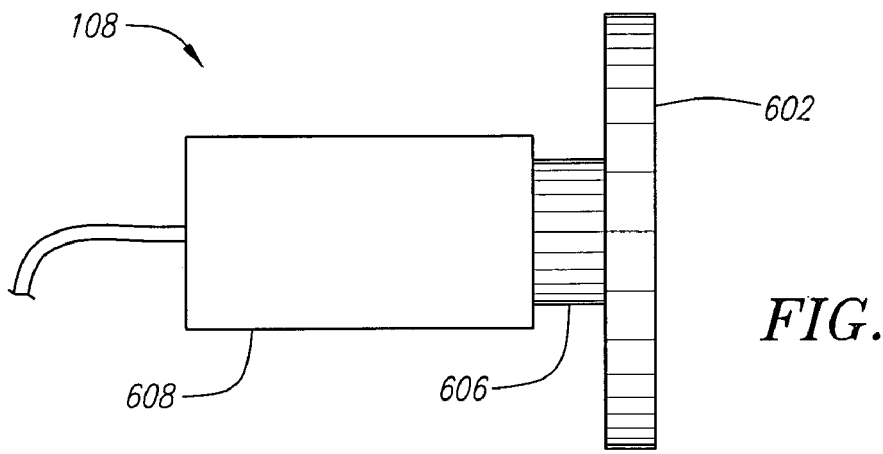
FIG. 6a depicts a side view an embodiment of a camera and illuminator that can be utilized in the invention.
Figure 6B:
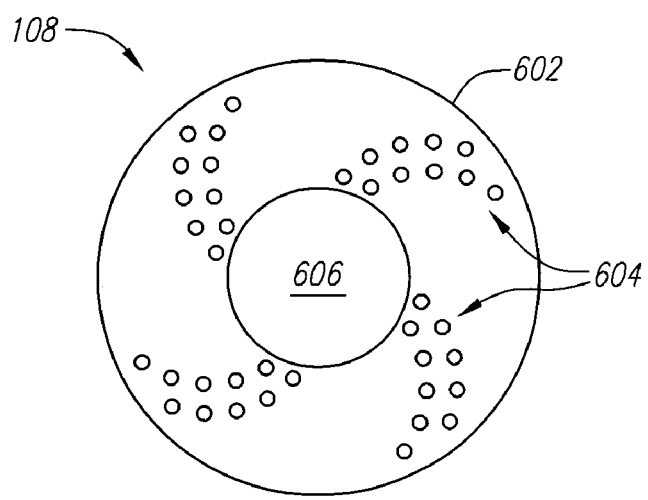

FIGS. 6a and 6b depict an embodiment of a camera 108 that can be used in the present invention to optically or visually collect data representative of breathing movement. Camera 108 is a charge-coupled device ("CCD") camera having one or more photoelectric cathodes and one or more CCD devices. A CCD device is a semiconductor device that can store charge in local areas, and upon appropriate control signals, transfers that charge to a readout point. When light photons from the scene to be imaged are focused on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to computer 110 to process the video image and to calculate the positions of the retro-reflective markers 114. According to an embodiment of the invention, camera 108 is a monochrome CCD camera having RS-170 output and 640×480 pixel resolution. In an alternate embodiment, camera 108 comprises a CCD camera having CCIR output and 756×567 pixel resolution.

In a particular embodiment of the invention, an infra-red illuminator 602 ("IR illuminator") is co-located with camera 108. If the IR illuminator 602 is located physically close to the camera 108, then camera 108 is positioned to capture strong reflections of IR reflected from retroreflective markers on the infant. IR illuminator 602 comprises a surface that is ringed around the lens 606 of camera body 608. The surface of IR illuminator 602 contains a plurality of individual infrared LED elements 604 for producing infrared light. The LED elements 604 are organized as one or more circular or spiral patterns on the IR illuminator 602 surrounding the camera lens 606. Infrared filters that may be part of the camera 108 are removed or disabled to increase the camera's sensitivity to infrared light.

According to an embodiment, digital video recordings of the infant can be recorded via camera 108. The same camera 108 used for tracking the infant's breathing movement can be used to record video images of the infant for future reference. A normal ambient light image sequence of the infant can be obtained in synchronization with the measured movement signals of markers 114.

Figure 7A:
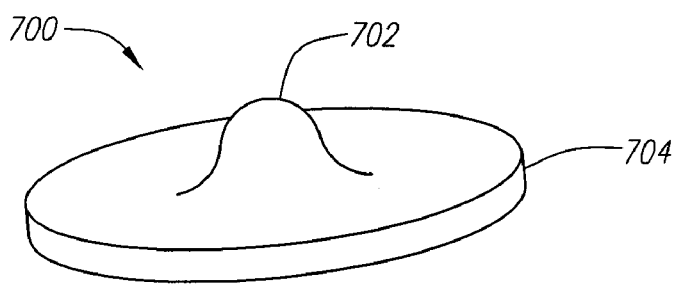
FIG. 7a depicts a retro-reflective marker according to an embodiment of the invention.
Figure 7B:
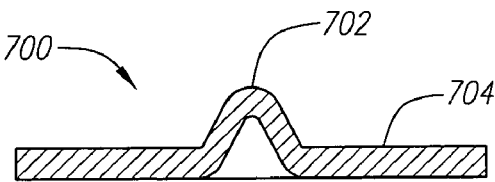

FIGS. 7a and 7b depict an embodiment of a retro-reflective marker 700 that can be employed within the present invention. Retro-reflective marker 700 comprises a raised reflective surface 702 for reflecting light. Raised reflective surface 702 comprises a semi-spherical shape such that light can be reflected regardless of the input angle of the light source. A flat surface 704 surrounds the raised reflective surface 702. The underside of flat surface 704 provides a mounting area to attach retro-reflective marker 700 to particular locations on an infant's body. According to an embodiment, retro-reflective marker 700 is comprised of a retro-reflective material 3M™ High-Gain Sheeting 7610WS available from 3M Corporation. In an embodiment, marker 700 has a diameter of approximately 0.5 cm and a height of the highest point of raised reflective surface 702 of approximately 0.1 cm. Alternatively, a marker can comprise a circular, spherical, or cylindrical shape.

In an alternate embodiment, marker 114 comprises a rigid marker block having one or more reference locations on its surface. The marker block is used in place of, or in addition to, the individual retro-reflective markers 114 to detect particular locations on an infant's body with an optical imaging apparatus. Each reference location on the marker block preferably comprises a retro-reflective or reflective material that is detectable by an optical imaging apparatus, such as camera 108. The retro-reflective elements can be formed from the same material used to construct retro-reflective markers 114 of FIGS. 7a and 7b. The marker block is preferably formed from a material that is light-weight enough not to interfere with normal breathing by an infant.

A marker block can be formed into any shape or size, as long as the size, spacing, and positioning of the reference locations are configured such that a camera or other optical imaging apparatus can view and generate an image that accurately shows the positioning of the marker block. The marker block can be formed with shapes to fit particular body parts. For example, molds or casts that match to specific locations on the body can be employed as marker blocks. Marker blocks shaped to fit certain areas of the body facilitate the repeatable placement of the marker blocks at particular locations on the infant. Alternatively, the marker blocks can be formed to fit certain fixtures that are attached to an infant's body. In yet another embodiment, the fixtures are formed with integral marker block(s) having reflective or retro-reflective markers on them. An alternate embodiment of the marker block comprises only a single reference location/reflective element on its surface.

According to one embodiment of the invention, an infant's breathing movement can be detected by tracking retro-reflective markers attached to the marker block. As shown in FIG. 8c, one embodiment of the marker block 871 utilizes two markers 873 and 875 on a rigid hollow and light plastic block 877 measuring about 6 Cm×4 Cm×4 Cm. The two markers 873 and 875 are preferably placed at a fixed distance of three centimeter on the side of the block that will face the tracking camera. The fixed distance between the two markers 873 and 875 is known and is used to calibrate the motion of the block in the direction of the line connecting the two markers.

According to one embodiment, the pixel coordinates of each marker in the video frame are tracked. The distance in the pixel domain between the two markers for each video frame is thereafter measured. The known physical distance of the two markers is divided by the measured distance to provide the scale factor for transforming the incremental motion of the block in the direction of the line connecting the two markers. This scale factor is updated for each new video frame and transforms the incremental motion of each marker from pixel domain to the physical domain. The transformation accounts for changes in the camera viewing angle, marker block orientation, and its distance to the camera during motion tracking.

Figure 10:
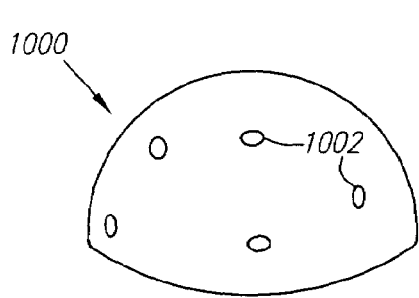
FIG. 10 depicts an embodiment of a hemispherical marker block.
Figure 11:
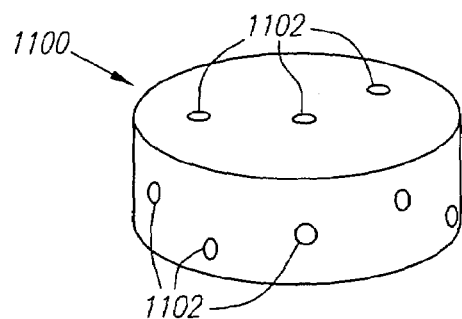
FIG. 11 depicts an embodiment of a cylindrical marker block.

FIG. 10 depicts an marker block 100 having a hemispherical shape comprised of a plurality of retro-reflective elements 1002 attached to its surface. FIG. 11 depicts alternate embodiment of a marker block 1100 having a cylindrical shape with multiple reference locations comprised of retro-reflective elements 1102 located on its surface.

Figure 8A:
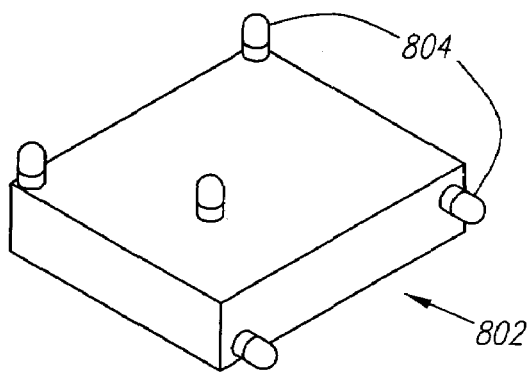
FIGS. 8a, 8b, and 8c depict embodiments of a marker block.
Figure 8B:
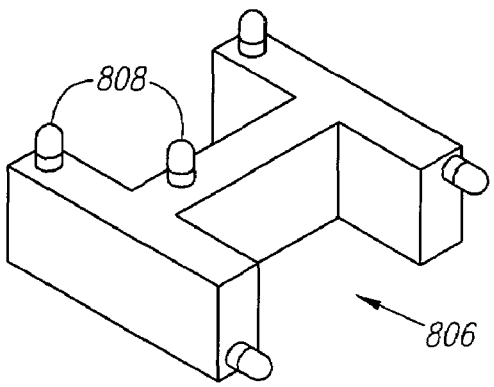
Figure 8C:
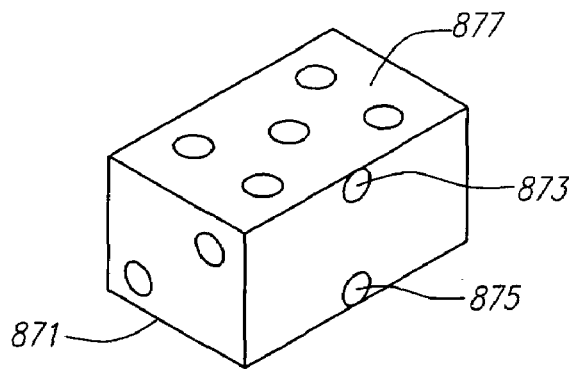

FIGS. 8*a* and 8*b* depict other embodiments of marker blocks 802 and 806 usable in the invention. Marker block 802 includes a rectangular shape having multiple reflective or retro-reflective marker elements 804 located on it. Marker block 802 supports a rigidly mounted set of markers 804 spread over an approximate volume of 1.5"×3"×4". The markers should appear as high contrast features in a real-time imaging device such as a video camera whose images are digitized and processed by a computer system. This realization of the marker block employs retro-reflective material covering a set of 0.25-inch diameter spheres glued or otherwise attached to a rigid plastic box or platform. Marker block 806 includes a non-rectangular structure having multiple reflective or retro-reflective marker elements 808 located on it. In an embodiment, the marker block is attached to an infant using adhesive tape.

An infant's respiration motion can be monitored by optical tracking of a marker block, such as a marker block 802 or 806, attached to an infant's chest, clothes, blanket, or other suitable locations that can reflect the infant's breathing motion. In operation, a camera or video view of the marker block produces a set of image coordinates for the marker elements on the marker block. The position and distance of any marker element located on the marker block is known relative to other marker elements on the same marker block. By comparing the position and distance between the marker elements on a recorded image frame with the reference position and image stored for the monitoring system, the absolute position and orientation of the marker block can be estimated with a high degree of accuracy. This, in turn, provides an accurate position and orientation estimation for the infant or infant body position upon which the marker block is attached. Note that estimation of infant position and orientation can be performed in the invention using only a single marker block, rather requiring the placement of multiple markers on different locations. Moreover, a single camera can be used to track the position of the marker block, rather than requiring triangulation using multiple cameras from different positions. A single-camera process for determining the precise position and orientation of the marker block with six degrees of freedom (6 DOF), i.e., x-coordinate, y-coordinate, z-coordinate, pitch, yaw, and roll is disclosed in co-pending U.S. application Ser. No. 10/234,658, filed Sep. 3, 2002, which is hereby incorporated by reference in its entirety. A single camera approach to track an object is also disclosed in U.S. application Ser. No. 09/893,122 filed Jun. 26, 2001, which is also incorporated by reference in its entirety.

A sleeping infant can move or roll into another position such that one or more markers attached to the infant (or attached to a marker block) fall outside the field of view of camera 108. Consequently, the infant's breathing movement may no longer be detected, and reporting irregularity in breathing activity that occurs thereafter becomes impossible. Thus, in an embodiment, failing to locate one or more markers in the image frame, system 100 will transmit an alarm signal to indicate a need to reposition the infant. This alarm signal is preferably distinguishable from an alarm that indicates a detected irregularity in the breathing activity. In an alternative embodiment, system 100 will transmit an alarm signal after being unable to locate one or more markers in two or more consecutive image frames. This can reduce the number of false alarms due to the sudden movement or coughing of the infant, who nonetheless returns back to a normal position thereafter.

Figure 9:
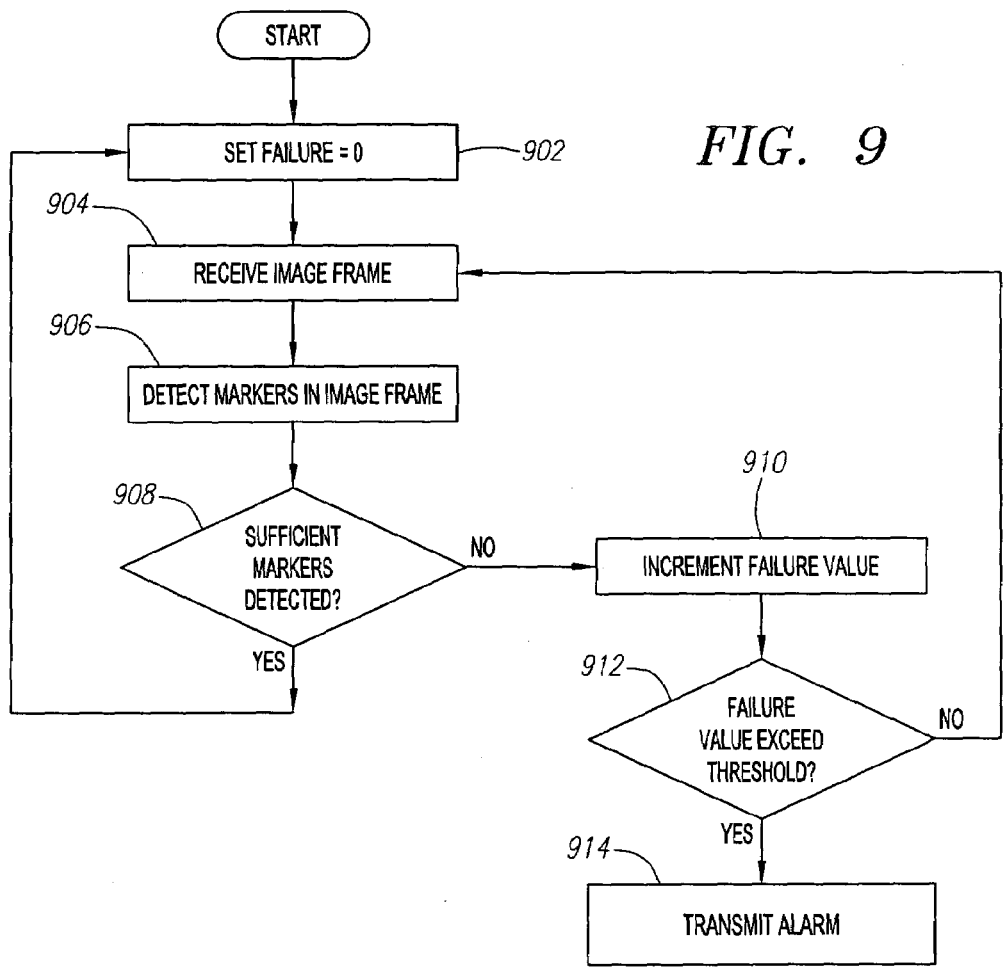
FIG. 9 shows a flowchart of a process for monitoring an infant according to an embodiment of the invention.

FIG. 9 shows a flowchart of a process for monitoring a patient by tracking a marker block according to an embodiment of the invention in which only a single camera is used to track the position and orientation of the marker block. In this approach, a subset of three or more markers on a marker block should be visible in an image frame to allow proper identification and calculation of the position and orientation for the marker block. This subset in the invention can vary from frame to frame in the input video stream. If a subset of three or more markers is not identified in a number of consecutive image frames, then an assumption is made that the infant has rolled or shifted into another position, and an alarm signal is transmitted.

At step 902, a FAILURE value, which counts the number of consecutive failures to appropriately locate the markers in image frames, is set to zero. As previously stated, in one embodiment, this failure is identified by not being able to acquire three or more markers in an image frame. At step 904, an image frame is digitized from the camera video stream.

At step 906, the digitized image frame from step 904 is analyzed to detect and locate the markers in pixel coordinates. If the previous tracking was successful, use the projected centers to limit the search area for each marker to increase the computational efficiency. If processing the first image frame, recovering from lost track, or failing to locate marker(s) in the limited search area, then the whole frame is analyzed to find and locate markers.

At step 908, a determination is made whether sufficient markers were detected at step 906. If the marker block is found by the image analysis process at Step 906, the process next returns to step 902, where the FAILURE value is reset to zero, and then to step 904 is performed to the next image frame in the video stream.

If sufficient markers are not located by the image analysis process at 906, it will be assumed that the infant has moved or rolled to another position, and accordingly, the FAILURE value is incremented (910). In a preferable embodiment, if the FAILURE value has reached or exceeded a threshold value (e.g., a value of two, which indicates that the marker block cannot be located in two consecutive image frames in the video stream), an alarm signal is transmitted (914). The number of consecutive failures in locating the marker block that triggers an alarm signal can vary.

The process of FIG. 9 can also be employed with individual markers rather than markers on a marker block. Alternatively, the process can be employed to track markers on multiple marker blocks.

In one embodiment, a determination of the position and orientation data for the marker block can be correlated to determine the position and orientation of the infant to which it is attached. The measured movement of the marker block can be used as an indicator of the infant's respiration activity. Thus, quantifiable values such as amplitude and/or phase of the marker block movement can be generated to monitor the infant's breathing movement. These values can be displayed and analyzed for breathing patterns using any conventional algorithms. As described in more detail below, the amplitude and/or phase of the marker block and the detection of deviations from periodic breathing movement can be used to trigger an alarm signal.

Detection of Irregularity in Breathing Pattern

To monitor an infant's breathing activity, one or more sets of data representative of the breathing activity of interest are collected for the infant in an embodiment of the invention. An optical-based system, such as system 100 of FIG. 1 using marker(s) or a marker block, may be employed to generate data for breathing activity usable in the invention.

Figure 4:
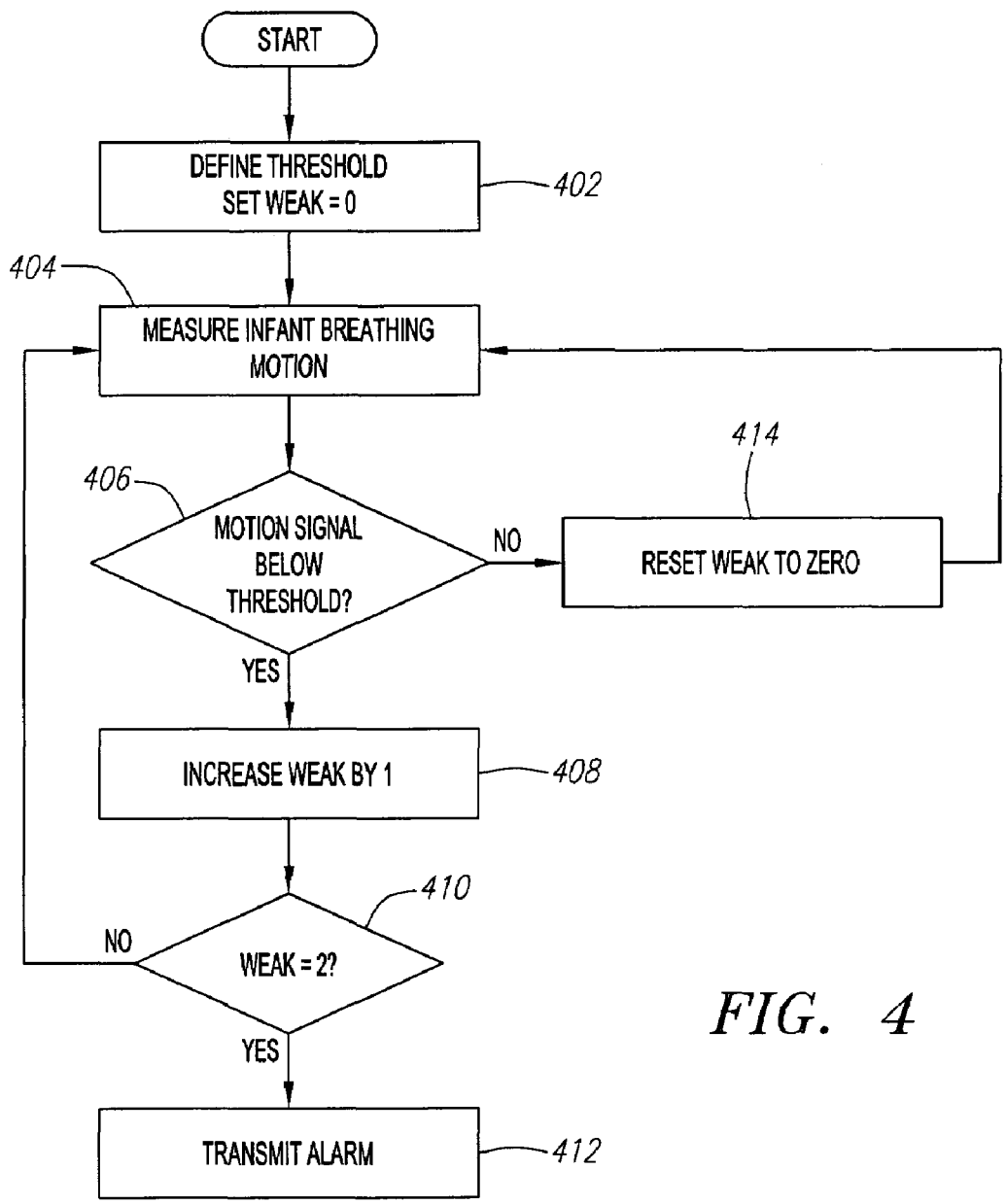
FIG. 4 is a flowchart showing process actions performed in an embodiment of the invention.

One aspect of the present invention provides a method to detect and report cessation of a breathing movement, indicating a likelihood of SIDS. FIG. 4 is a flowchart of the process actions in an embodiment of the invention to detect cessation of the breathing movement. The first process action is to define a threshold and to set variable WEAK that records the number of consecutive weak breathing signals (i.e. amplitude is below the defined threshold) to zero (402). An optical or video imaging system, such as a video camera, is used to measure the breathing motion of the infant (404). At step 406, an output signal of the optical or video imaging system is processed to compare the amplitude of the measured motion signal with the threshold defined in step 402.

If the amplitude of the motion signal is below the threshold, the breathing activity will be determined weak, and accordingly, variable WEAK will be increased by one. In a preferable embodiment, if two consecutive weak signals have been measured (i.e., WEAK=2), then the breathing activity is assumed to have ceased, and an alarm signal is thereby transmitted (412). However, the number of consecutive weak signals that triggers an alarm signal can be altered. A higher number renders the assumption of a ceased breath more accurate, but can potentially delay an alarm signal. In contrast, using a lower number tends to be more precautionary, but can be associated with an increased frequency of false alarm, often arising from weak signal that is merely momentary.

An amplitude of the motion signal exceeding the threshold is indicative of a strong breathing activity. As such, the process returns back to step 404 to measure new breathing motion signal, after resetting variable WEAK to zero at step 414.

One embodiment of the present invention provides a method for detecting a period of the respiration activity and deviation(s) from the periodicity. For example, sudden movement or coughing by an infant can result in deviation from the detected period of the respiration cycle. According to an embodiment, the present invention can "phase lock" to the respiration movement of the infant. Since the monitoring system phase locks to the breathing movement period, deviations from that periodic signal can be identified and appropriately addressed.

Figure 5:
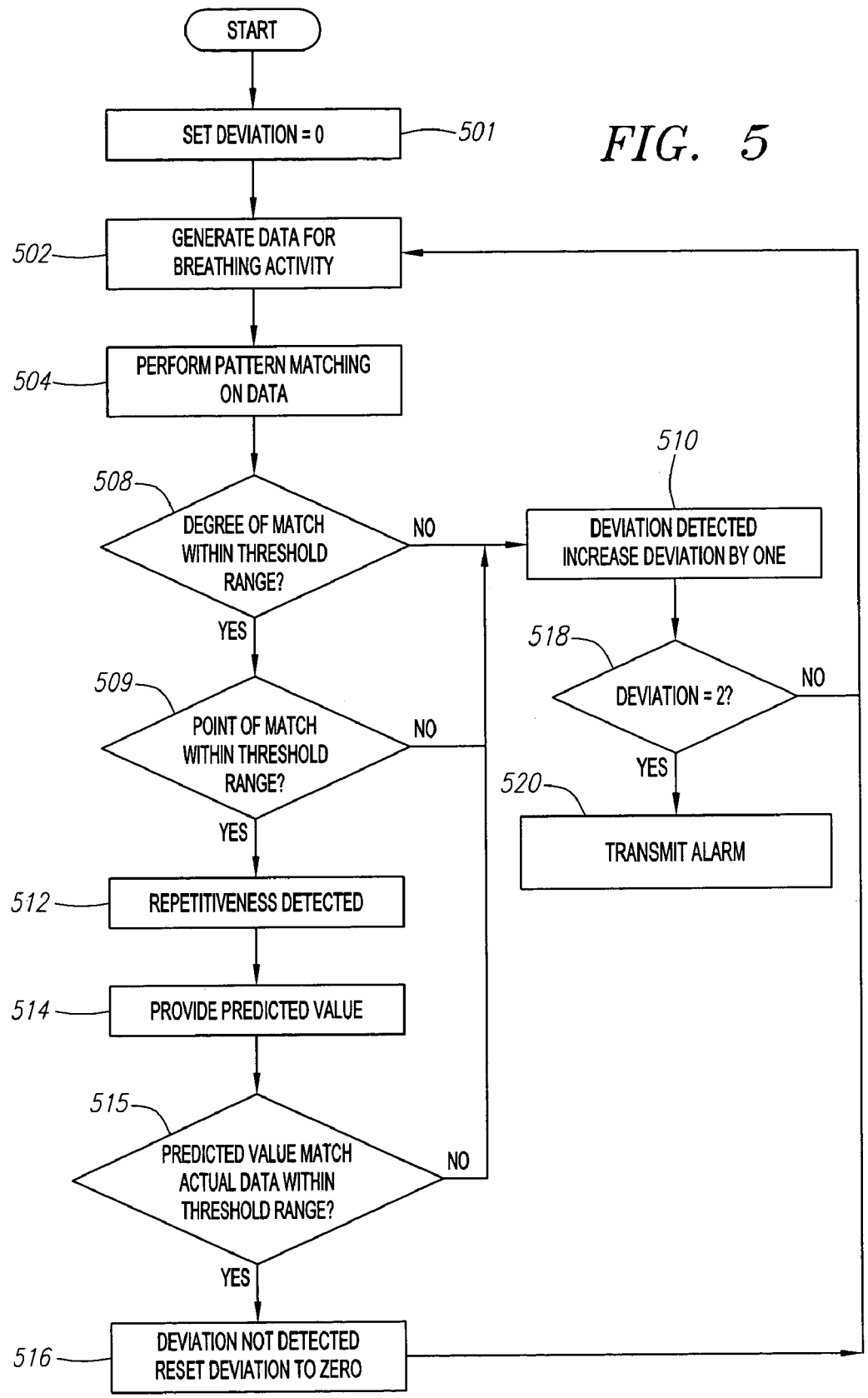
FIG. 5 is a flowchart showing process actions for detecting deviation(s) from regular breathing movement.

FIG. 5 is a process flowchart of an embodiment of the invention to perform predictive estimation and detection of regular respiration movement cycles and to identify deviation(s) from regular respiration movement. At the initial process action 501, variable DEVIATION that tracks the number of consecutive deviations (e.g., non-periodicity of the breathing activity) in an infant's breathing activity is set to zero. At process action 502, an instrument or system (such as system 100 from FIG. 1) is employed to generate data signals representative of the breathing activity of interest. In an embodiment, the data signals comprises a stream of digital data samples that collectively form a signal wave pattern representative of the breathing movement under examination. A number of discrete measurement samples are taken during a given time period. For example, in an embodiment of the invention, approximately 200–210 data samples are measured for each approximately 7 second time interval.

At process action 504, pattern matching analysis is performed against the measured data samples. In an embodiment, the most recent set of data samples for the breathing signal is correlated against an immediately preceding set of data samples to determine the period and repetitiveness of the signal. An autocorrelation function can be employed to perform this pattern matching. For each new sample point of the breathing motion, the process computes the autocorrelation function of the last n samples of the signal, where n corresponds to approximately 1.5 to 2 signal breathing periods. The secondary peak of the autocorrelation function is then identified to determine the period and repetitiveness of the signal.

In an alternate embodiment, an absolute difference function is used instead of an autocorrelation function. Instead of secondary peak, a secondary minimum in the absolute difference is searched for. For each new sample point of the breathing motion, the process computes the minimum absolute difference between the two sets of data over a range of overlapping data samples. The secondary minimum corresponds to the data position that best matches the recent set of data samples with the preceding set of data samples.

Yet another alternate embodiment performs a pattern matching based upon a model of the breathing activity being measured. The model is a dynamic representation of the breathing motion. The latest set of data samples is matched against the model to estimate parameters of the repetitive process. According to an embodiment, the model can be periodically updated to reflect changes in infant position and orientation as well as other changes that can result in alternation in the infant's breathing pattern. For example, temperature in the infant's bedroom may have impact on the period of the breathing movement.

Pattern matching using the measured breathing signal (504) provides information regarding the degree of match, as well as a location of best match for the repetitive process. If an autocorrelation function is employed in process action 504, then the relative strength of secondary peak provides a measure of how repetitive the signal is. A threshold range value is defined to provide indication of the degree of match between the two sets of data samples. If the strength of the secondary peak is within the defined threshold range (process action 508), then the degree of match indicates that the signal is repetitive, and the secondary peak location provides an estimate of the signal period. If an absolute difference function is used in process action 504, then the relative value of the secondary minimum provides a measure of how repetitive the signal is. If the value of the secondary minimum meets a defined threshold range (508), then the degree of match indicates that the signal is repetitive, and the secondary minimum location provides an estimate of the signal period.

If the correlation value of the secondary peak or secondary minimum does not meet the defined threshold range, then a deviation from the regular breathing activity is detected, thereby indicating possible irregularity in the breathing activity of the infant. This irregularity could result, for example, re-inhaling of the exhaled carbon dioxide. In an embodiment, an alarm signal is transmitted once a deviation is detected. In a preferable embodiment as shown in FIG. 5, variable DEVIATION is increased by one if a deviation is detected (510). After deviations are detected in two consecutively measured data samples (518), a presence of irregularity in the breathing activity is assumed and an alarm signal is therefore transmitted (520). Depending on preferences and particular requirements, however, the number of consecutive deviations that trigger an alarm can vary. For example, a higher number, at the expense of delaying an alarm, can render the assumption of irregularity more accurate.

If the degree of match indicates repetitiveness, the point of best match is tested to determine if the period is within a reasonable range. The location of the secondary peak or secondary minimum provides an estimate of the period of the breathing activity. In an embodiment, the point of best match is compared to a threshold range (509). If the point of best match does not fall within the threshold range, then a deviation from regular breathing activity is detected and the process proceeds to process action 510. If the point of best match falls within the threshold range, then the signal is accepted as being repetitive (512).

The estimate of the period based on the point of best match can be used to predict the period and waveform parameters of the next set of data samples for the signal (514). Note that process actions 504, 508, and 509 test for repetitiveness based upon a plurality of data samples over a range of such samples. However, in some circumstances, a significant deviation from normal breathing movement may actually occur within the new or most recent data sample(s) being analyzed, but because the overall set of data samples indicates repetitiveness (e.g., because of averaging of absolute differences over the range of data samples being compared), process actions 504, 508, and 509 may not detect the deviation. To perform a test for rapid deviation, the predicted value from process action 514 is compared with the next corresponding data sample (515). If the predicted value does not match the actual data sample value within a defined threshold range, then a deviation is detected and the process proceeds to process action 510. If a comparison of the predicted and actual data sample values fall within the defined threshold range, then repetitiveness is confirmed, and deviation is not detected for that data sample range (516). Accordingly, variable DEVIATION will be set to zero, and the process returns to process action 502 to measure new data signal.

In an embodiment, the first time the process of FIG. 5 is performed, the pattern matching process action (504) is performed over the entire range of data samples. Thereafter, the pattern matching process action can be performed over a limited search interval, which is defined by the results of the prior immediate execution of the process. For example, the predicted value from process action 514 can be used to define the location of the search interval for the next set of data samples. However, if process action 508, 509, and 514 detect deviation based upon analysis of the initial search interval, then the search interval can be expanded to ensure that a deviation has actually occurred. The process of FIG. 5 can be repeated with the increased search interval to attempt to find a point of best match outside of the initial search interval. In an embodiment, this increased search interval comprises the entire range of data samples. Alternatively, the increased search interval comprises only an expanded portion of the entire range of data samples.

Figure 3A:
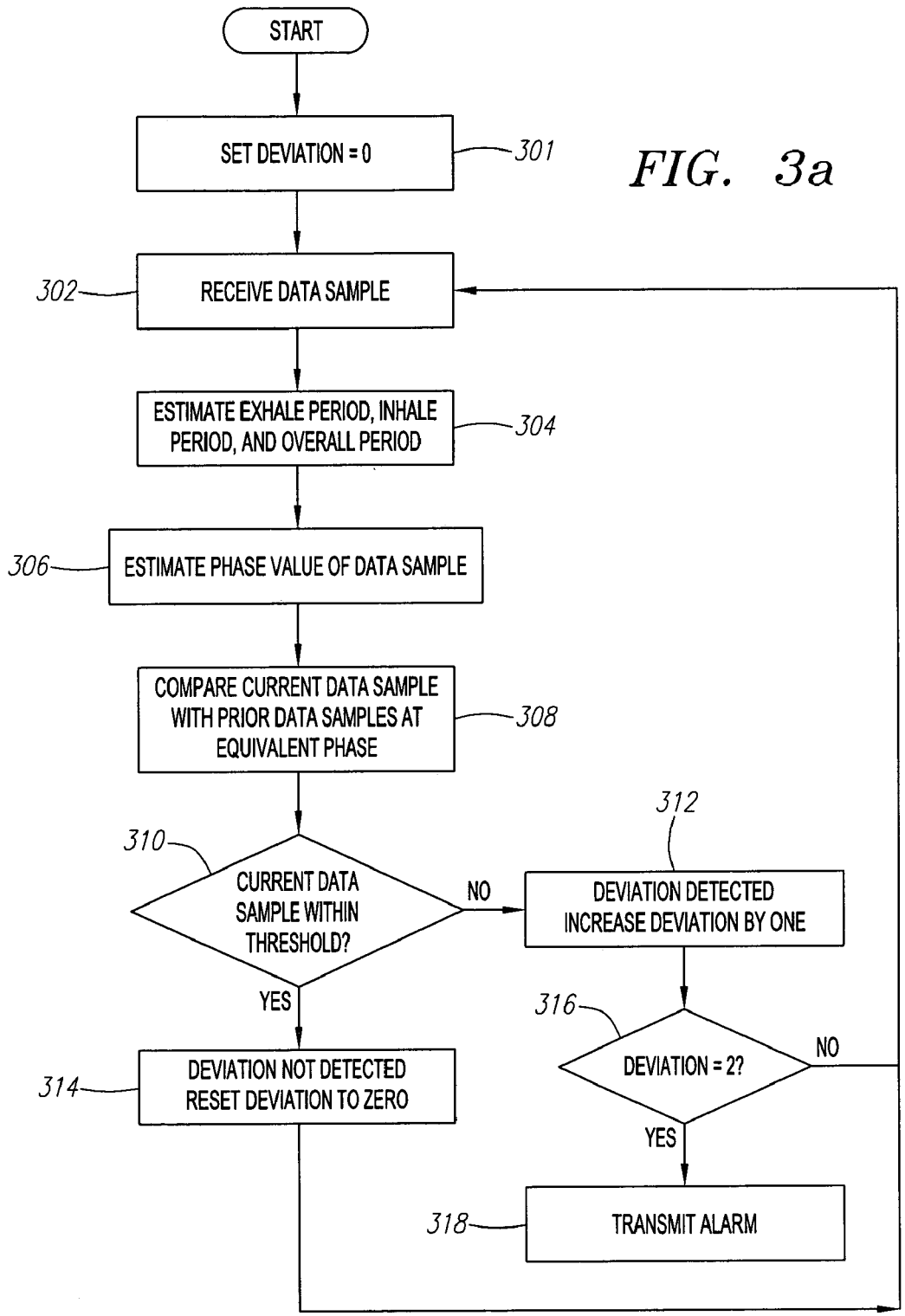
FIG. 3a shows a flowchart of a process for detecting periodicity or lack of periodicity according to an embodiment of the invention.
Figure 3B:
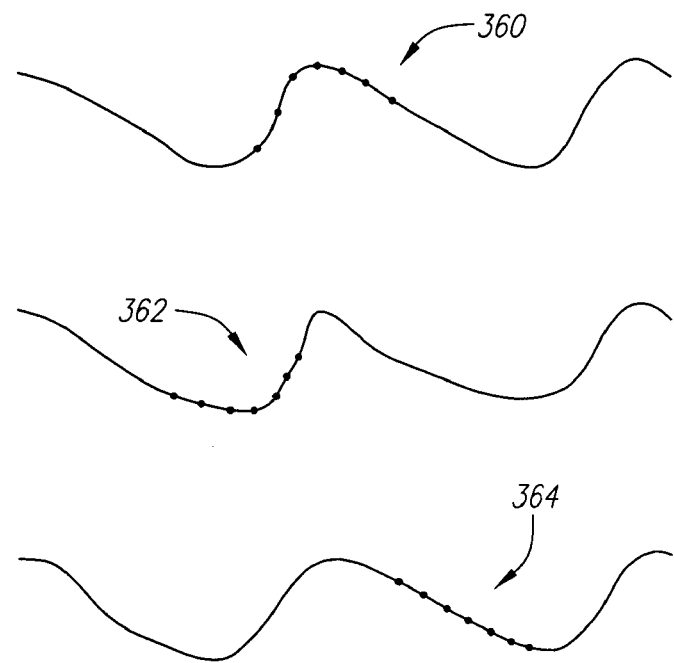
FIG. 3b illustrates sample trains according to an embodiment of the invention.
Figure 3C:
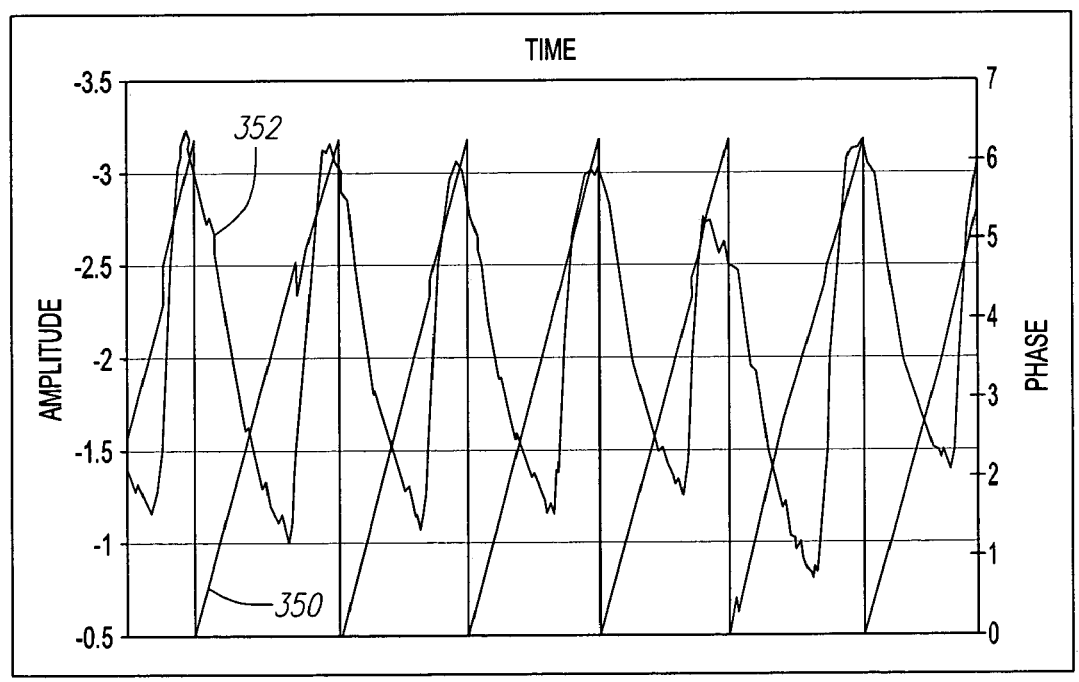
FIG. 3c is an example chart of showing phase and amplitude for a periodic signal.

FIG. 3a shows a flowchart of an alternative approach for detecting deviation from periodicity of a respiration activity. This process tracks the phase of a periodic signal, and for each breathing signal sample, this approach provides an estimate of phase value indicating the breathing cycle phase for an infant. In the embodiment described here, the phase angles ranges from 0 to $2\pi$ (0 to 360 degrees) with 0 and $2\pi$ corresponding to the vicinity of inhale extreme of the respiration signal. FIG. 3c shows an example phase value chart 350 for breathing signal samples superimposed on an example respiration amplitude signal 352.

The initial step 301 of FIG. 3a sets variable DEVIATION to zero that reflects the number of consecutive deviations in the infant's breathing movement. The process receives a respiration data sample at step 302. For each new sample of the respiration signal, the process obtains and updates estimates of the latest inhale and latest exhale extreme values and corresponding time points of the respiration signal. These values are used to establish the latest estimates of exhale period, inhale period, and therefore T, the overall period of breathing (304).

At step 306, the process estimates the phase value of the newly acquired respiration signal sample. In an embodiment, this is performed by computing the inner product of a Cosine waveform with period T (estimated at step 304) and the most recent T-seconds-long segment of the signal. This is repeated by computing the inner product with a Sine waveform of period T. These two inner products are called, respectively, the in-phase and quadrature components of the signal. The inverse Tangent of the result of dividing the quadrature value by the in-phase value provides the estimated phase for the current respiration signal sample.

Figure 3D:
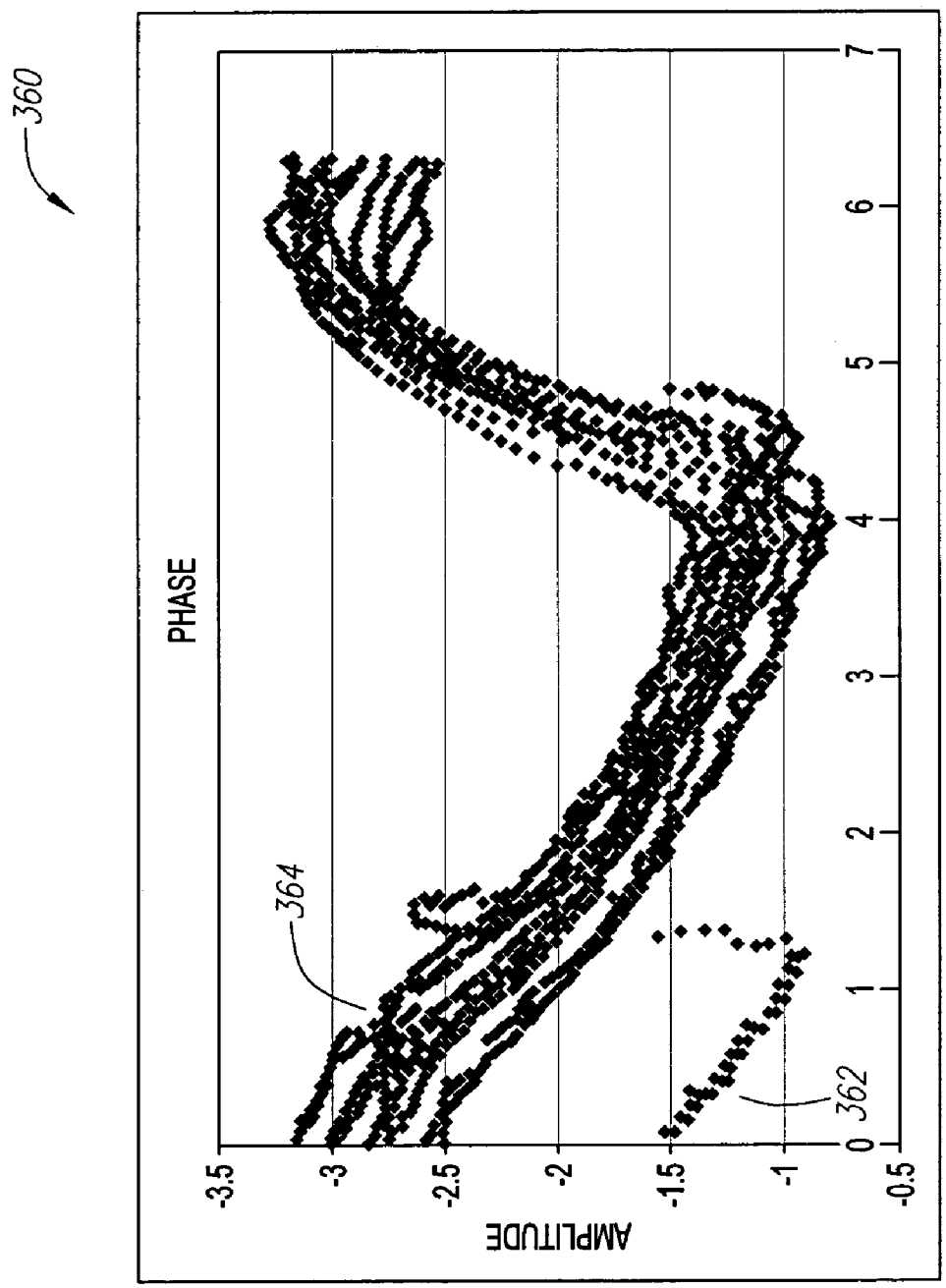
FIG. 3d shows an example of a periodic signal amplitude-phase histogram chart.

At step 308, the process compares the vector, e.g., (amplitude, phase), of the current respiration sample with previous data sample values to determine periodicity of the signal. One approach to performing this comparison step is to use a two-dimensional histogram array of signal vs. phase value that is accumulated during prior recordings of the respiration signal. FIG. 3d shows an embodiment of a 2-dimensional histogram array 360 of amplitude-phase values. Histogram array 360 is a 64×64 array of bins covering the 0 to $2\pi$ phase in the horizontal dimension and the range of respiration signal amplitude in the vertical dimension. The amplitude and estimated phase of each new sample are used to increment the corresponding bin in histogram array 360.

In an embodiment, a clustering factor determines how close the current respiration data sample vector is to the cluster of values observed so far. By comparing the amplitude-phase vector of each signal sample with the cluster of prior values in its neighborhood at step 310, the process provides a measure of periodicity for the signal. The signal is considered non-periodic for the current sample time when the clustering factor is below a defined threshold or tolerance level (312). Otherwise the signal is declared periodic (314). One approach is to calculate the sum of the bin populations for the 8-amplitude×5-phase surrounding bins for the current data sample. This population, as a percentage of the total population of all histogram bins accumulated so far, determines the degree to which the new sample belongs to a periodic signal. By applying a threshold to this percentage value, the signal sample is declared as periodic or non-periodic. This threshold value can be set by the user as the sensitivity of the algorithm for detecting deviations from periodicity. In the example of FIG. 3d, data sample set 362 would presumably be declared as non-periodic since it substantially departs from the general body of data sample values 364, assuming that the values in data sample set 362 cause the determined percentage value to exceed a defined threshold.

According to one embodiment, once the signal is determined as being non-periodic (i.e. deviation from periodicity), irregularity in the breathing pattern is detected and an alarm signal is transmitted. To improve the reliability of the results, in a preferable embodiment as shown in FIG. 3a, variable DEVIATION is incremented by one if a deviation from periodicity is detected. After deviations from periodicity are identified in two consecutive data samples (316), a presence of irregularity in the breathing activity is assumed and an alarm signal is thereby transmitted (318). Depending on preferences and particular requirements, however, the number of consecutive deviations that triggers an alarm can be altered.

If the signal is considered periodic for the current sample time, the process will return to the step 302 to receive new data sample, after resetting variable DEVIATION to zero.

According to an embodiment, estimation of the inhale and exhale periods pursuant to step 304 of FIG. 3a begins by identifying a starting assumption of these periods. If the process is at its very beginning, or is recovering from a loss of periodicity, then nominal or default values (such as inhale period=1.6 Sec and exhale period=3.4 Sec) are used. The sum of these values is the current estimate of the breathing movement period. The approach of the present embodiment uses the most recent n samples of the signal to estimate the location and value of the minimum and maximum values, e.g., caused by breathing motion. One embodiment selects seven samples by sub-sampling the signal at intervals of $1/20^{th}$ of the period. The choice of seven samples makes the computational load of the interpolation process manageable, while sub-sampling allows coverage of a larger portion of the signal thus avoiding false detection of local minima and maxima due to noise. For every new sensed signal sample (not sub-sampled) the n samples selected as described above are first validated to make sure their corresponding interval includes a minimum or a maximum. This is performed by comparing the absolute difference of the two end samples of the sample train with the average of the difference of the center sample and the two end samples. One embodiment uses the test:

$$Abs(Y(0)-Y(6))<0.2*Abs(Y(0)+Y(6)-2*Y(3))$$

to determine whether the sample train includes a minimum or a maximum. In this example the train of seven samples, Y(0), Y(1), Y(2), Y(3), Y(4), Y(5), Y(6), are sub-sampled at $1/20^{th}$ of the of the number of samples constituting the current estimate of one period. If the result of this test is positive, curve fitting to the samples is performed. One embodiment fits a quadratic curve to the middle five points of the seven-point sample train. The location and value of the minimum or maximum value of this curve is computed using interpolation. Also at this point, it is determined whether the estimated point is a minimum or a maximum by comparing the end samples of the train with the middle sample. The estimated location of the minimum or maximum points are added to their respective accumulator variables for later averaging.

The above process is repeated with the next sensed signal sample until the procedure encounters the first sample for which the above test result is negative. This is an indication that the run of points for which a minimum or maximum can be estimated has ended. At this point the accumulator variables are divided by the number of points in the run to obtain the average location and value from the run.

The process continues by repeating the above test on the sample-train preceding every new sensed signal sample. Once the test result is positive the averaging process described above will start again. FIG. 3b shows three examples of sample trains; sample train 360 includes a local maximum; sample train 362 includes a local minimum; and, sample train 364 includes neither a maximum nor a minimum.

This method estimates the local minimum or maximum location at a point in time that is later than the actual position of the extremum by the length of the sample train. The current estimate of the inhale or exhale period is updated at this point in time. For inhale period, for example, this is performed by subtracting the latest maximum position from the latest minimum position in time. These estimates are used to update the current value of the total period.

The embodiments described herein provides a tool for measuring the periodicity of the respiration signal, thus allowing detection of deviation from normal breathing. This can be used to trigger the alarm during monitoring of breathing movement of an infant.

Monitoring Multiple Subjects

Figure 12:
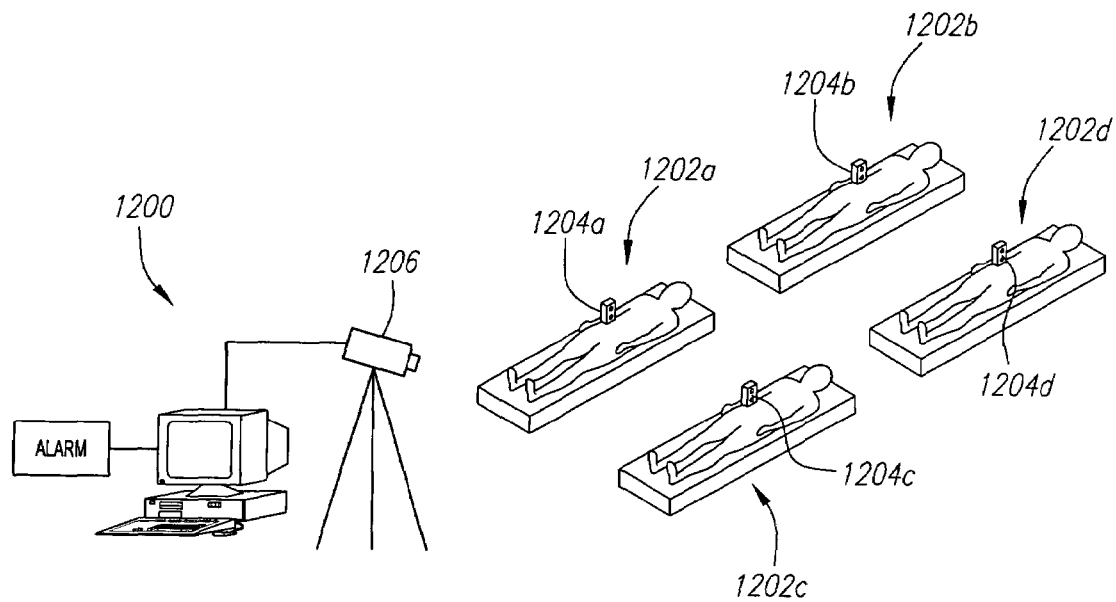
FIG. 12 shows a system for tracking movement of multiple subjects according to an embodiment of the invention.

Referring to FIG. 12, shown is an embodiment of the invention in which multiple subjects 1202a-d are monitored using optical monitoring system 1200. Each subject is associated or attached to a marker block 1204a-d, or a set of individual markers (not shown). The processes described above are performed to monitor each subject to detect an irregularity in the movement or breathing pattern of any of the subjects.

The system 1200 is set up such that the field of view for camera 1206 is appropriately configured to view the markers or marker blocks for all of the subjects for which monitoring is desired. If a single camera approach is being used to determine the position and orientation of a subject, then the configuration can be established such that at least three markers should be visible for each subject being monitored. If the field of view for camera 1200 is insufficiently large to view all the subjects, then additional cameras can be used to increase the view of view. In one approach, the subjects are divided into subgroups of subjects, with a camera associated with each sub-group. Each camera is configured to monitor the subjects in a particular location/area in the monitoring location. The sub-groups are established based upon the specific location of its subjects relative to the cameras.

In operation, camera 1206 would capture image frames containing images of the visible markers for subjects being monitored. For example, if four subjects are being monitored, then the four sets of markers (e.g., corresponding to markers blocks 1204a-d) are captured in the image frames.

One action that is performed when performing concurrent monitoring of multiple subjects is to associated the sets of markers identified in the image frame to the appropriate subjects. In one embodiment, the identification of each marker with a subject is performed by a user of the system 1200. This can be accomplished by implementing a GUI in which the user could link a particular marker or set of markers to a subject. This approach is useful, for example, when using isolated markers not located on a marker block.

The process to associate identified markers in the image frames with their corresponding subjects can be automated. For example, when using marker blocks, to associate a subject with its respective marker block(s), the computing system takes groups of markers, with the number of markers in the group the same as the number of markers on each block, and attempts to estimate a consistent and reasonable position and orientation for the block. Each possible or projected combination can be attempted and checked for a suitable match. A determination can be made of the markers that are associated with specific marker blocks by making an exhaustive attempt for all combinations.

Once each marker or set of markers has been associated with a subject, each set of markers for each subject can be individually processed to perform the monitoring. Thus, the images of the markers for marker block 1204*a* are processed to monitor the movement of subject 1202*a*, the images of the markers for marker block 1204*b* are used to monitor the movement of subject 1202*b*, and the images of the markers for marker blocks 1204*c* and 1204*d* are used to monitor the movement of subjects 1202*c* and 1202*d*, respectively. Any or all of the previously described processes can be employed to monitor the subjects. For instance, the processes described with respect to FIGS. 3*a* 4, 5, and/or 9 can be individually performed against a set of marker blocks for a subject. In addition, the process to determine the position and orientation of an object can be individually performed for each detected set of markers, as disclosed in co-pending U.S. application Ser. No. 10/234,658, filed Sep. 3, 2002 and U.S. application Ser. No. 09/893,122 filed Jun. 26, 2001, which are hereby incorporated by reference in their entirety.

It is noted a similar approach can be taken to monitor multiple marker blocks on a single subject. Multiple marker blocks can be used to simultaneously monitor the movement of multiple different positions on a single subject.

Figure 13:
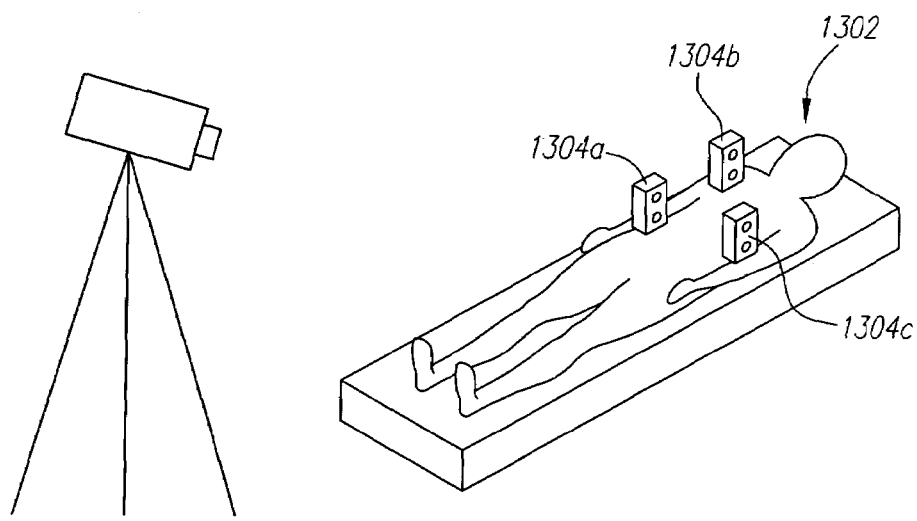
FIG. 13 shows a system for tracking movement of multiple marker blocks on a subject according to an embodiment of the invention.

Referring to FIG. 13, shown is a subject 1302 that is associated or affixed to multiple marker blocks. In particular, a first marker block 1304*a* is affixed to the lower torso, a second marker block 1304*b* is affixed to the upper torso, and a third marker block 1304*c* is affixed to the upper arms/shoulder of subject 1302.

The action described above to associate markers to marker blocks can be used to correspond individual markers to marker blocks, which are associated with respective body locations. Each set of markers is then individually processed to independently monitor the movements and/or location of its associated marker block. One advantage provided by this approach is that different alarm/error threshold levels can be configured for the different marker blocks, while still allowing simultaneous monitoring with a single camera system. This is advantageous since different parts of the subject may be subject to different types and ranges of movements and movement irregularities. Another advantage is that more precise measurements can be made of the location and movement of the subject or specific locations on the subject. Instead of having a single marker block used to determine the location/movement of a relatively large body region, multiple marker blocks are used to define smaller granularity body regions to measure.

In one embodiment, a system is implemented in which multiple subjects are monitored, in which one or more of the monitored subjects are associated with multiple marker blocks. Similar procedures are followed to associate the markers to marker blocks, and the marker blocks to respective body locations. However, multiple marker blocks are associated with the same subject to monitor different body locations on the subjects.

It is noted that while certain embodiments described herein specifically address monitoring of infants, the disclosed invention is applicable to monitor a broad range of possible subjects. For example, the inventive concepts can be applied to monitor the movement of other patients, including adult patients. Moreover, the invention could also be applied to monitor the regular/periodic movements of non-human subjects, such as animals or non-living subjects such as machinery.

In the foregoing specification, the invention has been described with reference to specific embodiments thereof. It will, however, be evident that various modifications and changes may be made thereto without departing from the broader spirit and scope of the invention. For example, the operations performed by computer 110 can be performed by any combination of hardware and software within the scope of the invention, and should not be limited to particular embodiments comprising a particular definition of "computer". Similarly, the operations performed by alarm device 116 can be performed by any combination of hardware and software within the scope of the invention, and should not be limited to particular embodiments comprising a particular definition of "alarm device". The specification and drawings are, accordingly, to be regarded in an illustrative rather than restrictive sense.

The invention claimed is:

1. A method of monitoring breathing activity, comprising:
    using an optical device to obtain a set of signal data representative of a breathing movement of a first patient during a time period;
    comparing amplitude of the set of signal data with a threshold; and
    reporting irregularity based upon a result of the comparison.

2. The method of claim 1 in which the step of reporting irregularity comprises transmitting an alarm signal.

3. The method of claim 1 in which the irregularity comprises measurement of a set of signal data, the amplitude of the set of signal data below the threshold.

4. The method of claim 1 in which the irregularity comprises measurement of two or more consecutive sets of signal data, the amplitudes of the two or more sets of signal data below the threshold.

5. The method of claim 1 in which the breathing movement is for an infant.

6. The method of claim 1, wherein the optical device is used to sense a marker on a marker block placed on a patient.

7. The method of claim 1, wherein the set of signal data is also representative of a breathing movement of a second patient.

8. The method of claim 1, wherein the amplitude is compared with the threshold to determine whether there is a deviation from periodicity of the breathing movement.

9. The method of claim 1, further comprising:
    determining a number of markers in an image provided by the optical device; and
    comparing the number of markers with a threshold value.

10. The method of claim 9, further comprising generating a signal when the number of markers is less than the threshold value.

11. The method of claim 1, wherein the irregularity is considered to have occurred when the amplitude exceeds the threshold.

12. The method of claim 1, wherein the irregularity is considered to have occurred when the amplitude is below the threshold.

13. A system for monitoring breathing activity, comprising:
- an optical device for measuring a set of signal data representative of a breathing movement during a time period;
- means for comparing amplitude of the set of signal data with a threshold; and
- means for reporting irregularity based upon a result of the comparison.

14. The system of claim 13 in which the means for reporting irregularity is configured to transmit an alarm signal.

15. The system of claim 13 in which the irregularity comprises measurement of a set of signal data, the amplitude of the set of signal data below the threshold.

16. The system of claim 13 in which the irregularity comprises measurement of two or more consecutive sets of signal data, the amplitudes of the two or more sets of signal data below the threshold.

17. The system of claim 13, wherein the optical device is used to sense a marker on a marker block placed on a patient.

18. The system of claim 13, wherein the means for comparing compares the amplitude with the threshold to determine whether there is a deviation from periodicity or the breathing movement.

19. The system of claim 13, further comprising:
- means for determining a number of markers in an image provided by the optical device; and
- means for comparing the number of markers with a threshold value.

20. The system of claim 19, further comprising means for generating a signal when the number of markers is less than the threshold value.

21. A computer program product that includes a medium usable by a processor, the medium having a set of instructions, an execution of which by a processor will cause a process to be performed, the process comprising:
- obtaining a set of signal data representative of a breathing movement during a time period, wherein the step of obtaining is performed using an optical device;
- comparing amplitude of the set of signal data with a threshold; and
- reporting irregularity based upon a result of the comparison.

22. The computer program product of claim 21 in which the step of reporting irregularity comprises transmitting an alarm signal.

23. The computer program product of claim 21 in which the irregularity comprises measurement of a set of signal data, the amplitude of the set of signal data below the threshold.

24. The computer program product of claim 21 in which the irregularity comprises measurement of two or more consecutive sets of signal data, the amplitudes of the two or more sets of signal data below the threshold.

25. The computer program product of claim 21, wherein the amplitude is compared with the threshold to determine whether there is a deviation from periodicity of the breathing movement.

26. The computer program product of claim 21, wherein the process further comprises:
- determining a number of markers in an image provided by the optical device; and
- comparing the number of markers with a threshold value.

27. The computer program product of claim 26, wherein the process further comprises generating a signal when the number of markers is less than the threshold value.

* * * * *

UNITED STATES PATENT AND TRADEMARK OFFICE
CERTIFICATE OF CORRECTION

PATENT NO. : 7,123,758 B2 Page 1 of 1
APPLICATION NO. : 10/327603
DATED : October 17, 2006
INVENTOR(S) : Andrew Jeung et al.

It is certified that error appears in the above-identified patent and that said Letters Patent is hereby corrected as shown below:

In column 7, line 20, delete 100 and replace with 1000

Signed and Sealed this

Twenty Second Day of April, 2008

JON W. DUDAS
*Director of the United States Patent and Trademark Office*